US012583915B2

(12) United States Patent
Kim et al.

(10) Patent No.: US 12,583,915 B2
(45) Date of Patent: Mar. 24, 2026

(54) METHODS FOR DIAGNOSING CANCER USING ANTI-BAG2 ANTIBODY

(71) Applicants: MEDPACTO, INC., Seoul (KR); YONSEI UNIVERSITY MEDICAL COLLEGE, GANGNAM SEVERANCE HOSPITAL, DEPARTMENT OF SURGERY, Seoul (KR); SUNGKYUNKWAN UNIVERSITY, DEPARTMENT OF BIOLOGICAL SCIENCES, Gyeonggi-do (KR)

(72) Inventors: Seong Jin Kim, Seoul (KR); Kyung-Min Yang, Incheon (KR); Joon Jeong, Seoul (KR); Sung Gwe Ahn, Seoul (KR); Seok Hee Park, Gyeonggi-do (KR); Dong Woo Kang, Seoul (KR)

(73) Assignees: Medpacto, Inc., Seoul (KR); Yonsei University Medical College, Gangnam Severance Hospital, Dept of Surgery, Seoul (KR); Sungkyunkwan University, Dept of Biological Sciences, Suwon (KR)

( * ) Notice: Subject to any disclaimer, the term of this patent is extended or adjusted under 35 U.S.C. 154(b) by 1173 days.

(21) Appl. No.: 16/758,934

(22) PCT Filed: Feb. 12, 2020

(86) PCT No.: PCT/IB2020/051139
§ 371 (c)(1),
(2) Date: Apr. 24, 2020

(87) PCT Pub. No.: WO2020/165797
PCT Pub. Date: Aug. 20, 2020

(65) Prior Publication Data
US 2023/0194534 A1     Jun. 22, 2023

(30) Foreign Application Priority Data

Feb. 12, 2019   (KR) ........................ 10-2019-0016347
Feb. 12, 2019   (KR) ........................ 10-2019-0016359

(51) Int. Cl.
| G01N 33/567 | (2006.01) |
| A61P 35/00 | (2006.01) |
| C07K 16/18 | (2006.01) |
| C12N 15/63 | (2006.01) |
| G01N 33/574 | (2006.01) |
| G01N 33/68 | (2006.01) |

(52) U.S. Cl.
CPC .............. *C07K 16/18* (2013.01); *A61P 35/00* (2018.01); *C12N 15/63* (2013.01); *G01N 33/57484* (2013.01); *G01N 33/6854* (2013.01); *C07K 2317/24* (2013.01); *C07K 2317/565* (2013.01); *G01N 2333/4703* (2013.01)

(58) Field of Classification Search
CPC ............... C07K 16/18; C07K 2317/24; C07K 2317/565; A61P 35/00; C12N 15/63; G01N 33/57484; G01N 33/6854; G01N 2333/4703
See application file for complete search history.

(56) References Cited

U.S. PATENT DOCUMENTS

| 2004/0063101 A1 | 4/2004 | Scanlan |
| 2006/0099144 A1 | 5/2006 | McClanahan |
| 2006/0159681 A1* | 7/2006 | Lozano .............. C07K 14/4747 |
| | | 424/143.1 |
| 2008/0292546 A1* | 11/2008 | Clarke ................. C12Q 1/6886 |
| | | 424/1.49 |
| 2009/0275608 A1 | 11/2009 | Ossovskaya et al. |
| 2010/0204055 A1* | 8/2010 | Bonner-Ferraby ... G01N 33/564 |
| | | 506/18 |
| 2010/0255470 A1* | 10/2010 | Bankaitis-Davis .. C12Q 1/6886 |
| | | 435/6.14 |

FOREIGN PATENT DOCUMENTS

| JP | 2007516693 A | 6/2007 |
| JP | 2011521618 A | 7/2011 |
| JP | 2017088519 A | 5/2017 |
| KR | 10-2018-0101052 A | 9/2018 |
| WO | 2018150031 A1 | 8/2018 |
| WO | 2019-083262 A1 | 5/2019 |

OTHER PUBLICATIONS

Yang et al.(Cell Reports 21:2952-2964; 2017; IDS ref). (Year: 2017).*
Notification of Transmittal of the International Search Report and the Written Opinion for corresponding PCT Application No. PCT/IB2020/051139, mailed May 26, 2020 (11 pages).
Yang, Kyung-Min, "Co-chaperone BAG2 determines the pro-oncogenic role of cathepsin B in triple-negative breast cancer cells", Cell Reports, (Dec. 5, 2017), vol. 21, No. 1010, doi: 10.1016/j.celrep.2017.11.026, ISSN 2211-1247, pp. 2952-2964, XP055595394.

* cited by examiner

*Primary Examiner* — Catherine S Hibbert
(74) *Attorney, Agent, or Firm* — FisherBroyles, LLP; Joseph Hyosuk Kim

(57) ABSTRACT

The present application discloses a composition for use in diagnosing cancer, the composition comprising: an antibody or antigen-binding fragment thereof that specifically binds to a BAG2 polypeptide or fragment thereof.

16 Claims, 14 Drawing Sheets
Specification includes a Sequence Listing.

2A11-3F12 pair

SEQUENCE LISTING

```
<160> NUMBER OF SEQ ID NOS: 74

<210> SEQ ID NO 1
<211> LENGTH: 369
<212> TYPE: DNA
<213> ORGANISM: Artificial Sequence
<220> FEATURE:
<223> OTHER INFORMATION: 2A11-VH

<400> SEQUENCE: 1
caggtccaac tgcagcagcc tggggctgag ctggtgaggc ctggggcttc agtgacgctg      60
tcctgcaagg cttcgggcta cacatttact gactatgaaa tgcactgggt gaagcagact     120
cctgtgcatg gcctggaatg gattggagtt attgatcctg aaactggtgc tactgcctac     180
aatcagaagt tcaagggcaa ggccacactg actgcagaca atcctccag tacagcctac      240 atggagctcc gcagcctgac atctgaggac tctgccgtct attactgtac aagagggaaa     300
ttttattact ccggtcggga ctatgctatg gactactggg gtcaaggaac ctcagtcacc     360
gtctcctca                                                            369

<210> SEQ ID NO 2
<211> LENGTH: 369
<212> TYPE: DNA
<213> ORGANISM: Artificial Sequence
<220> FEATURE:
<223> OTHER INFORMATION: 4C2-VH

<400> SEQUENCE: 2
caggtccaac tgcagcagcc tggggctgag ctggtgaggc ctggggcttc agtgacgctg      60
tcctgcaagg cttcgggcta cacatttact gactatgaaa tgcactgggt gaagcagact     120
```

-continued

```
cctgtgcatg gcctggaatg gattggagtt attgatcctg aaactggtgc tactgcctac        180
aatcagaagt tcaagggcaa ggccacactg actgcagaca atcctccag tacagcctac         240 atggagctcc gcagcctgac atctgaggac tctgccgtct attactgtac aagagggaaa        300
ttttattact ccggtcggga ctatgctatg gactactggg gtcaaggaac ctcagtcacc        360
gtctcctca                                                                 369

<210> SEQ ID NO 3
<211> LENGTH: 369
<212> TYPE: DNA
<213> ORGANISM: Artificial Sequence
<220> FEATURE:
<223> OTHER INFORMATION: 8C4-VH

<400> SEQUENCE: 3
caggtccaac tgcagcagcc tggggctgag ctggtgaggc ctggggcttc agtgacgctg         60
tcctgcaagg cttcgggcta cacatttact gactatgaaa tgcactgggt gaagcagact        120
cctgtgcatg gcctggaatg gattggagtt attgatcctg aaactgctgg tactgcctac        180
aatcagaagt tcaagggcaa ggccacactg actgcagaca atcctccag tacagcctac         240 atggagctcc gcagcctgac atctgaggac tctgccgtct attactgtac aagagggaaa        300
ttttattact ccggtcggga ctatgctatg gactactggg gtcaaggaac ctcagtcacc        360
gtctcctca                                                                 369

<210> SEQ ID NO 4
<211> LENGTH: 366
<212> TYPE: DNA
<213> ORGANISM: Artificial Sequence
<220> FEATURE:
<223> OTHER INFORMATION: 3B5-VH

<400> SEQUENCE: 4
gaggtccagc tgcaacagtc tggacctgag ctggtgaagc ctggggcttc agtgaagtta         60
tcctgcaagg cttctggtta ctcattcact gactacacct tttactgggt gaggcagagc        120
catggagaga gccttgagtg gattggatat attgatcctt acaatggtgg taatacttat        180
aaccggaagt tcaagggcaa ggccacattg actgttgaca agtcctccag cacagccttc        240
atgcatctca acagcctgac atctgaagac tctgcagtct attactgtgc gagagggtac        300
tataggtacg ggggggggg ggactttgac tactggggcc aaggcaccac tctcacagtc        360
tcctca                                                                    366

<210> SEQ ID NO 5
<211> LENGTH: 357
<212> TYPE: DNA
<213> ORGANISM: Artificial Sequence
<220> FEATURE:
<223> OTHER INFORMATION: 9B3-VH

<400> SEQUENCE: 5
gaggtccagc tgcaacaatc tggagctgag ctggtaaggc ctgggacttc agtgaaggtg         60
tcctgcaagg cttctggata cgccttcact aattacatga tagagtggat aaaacagagg        120
cctggacagg gccttgagtg gattggagtg attaatcctg aagtggtgg tagttattac         180 aatgagaagg tcaagggcaa ggcaacactg accgcagaca atcctccag cactgcctac         240 atgcagttca gcagcctgac agctgatgac tctgcggtct atttctgtcg gatctatggt        300
aactacaagg ggtactttga ctattggggc caaggcacca ctctcacagt ctcctca          357
```

```
<210> SEQ ID NO 6
<211> LENGTH: 357
<212> TYPE: DNA
<213> ORGANISM: Artificial Sequence
<220> FEATURE:
<223> OTHER INFORMATION: 9B12-VH

<400> SEQUENCE: 6
caggtccaac tgcagcagtc tggagctgag ctggtaaggc ctgggacttc agtgaaggtg      60
tcctgcaagg cttctggata cgccttcact aattacatga tagagtggat aaaacagagg     120
cctggacagg gccttgagtg gattggagtg attaatcctg gaagtggtgg tagttataac     180
aatgagaagg tcaagggcaa ggcaacactg accgcagaca gatcctccag cactgcctac     240
atgcagttca gcagcctgac agctgatgac tctggggtct atttctgtcg gatctatggt     300
aactacaagg ggtactttga ccattggggc caaggcacca ctctcacagt ctcctca        357

<210> SEQ ID NO 7
<211> LENGTH: 357
<212> TYPE: DNA
<213> ORGANISM: Artificial Sequence
<220> FEATURE:
<223> OTHER INFORMATION: 3B10-VH

<400> SEQUENCE: 7
caggtccaac tgcagcagcc tggagctgag ctggcaaggc ctgggacttc agtgaaggtg      60
tcctgcaagg cttctggcca cgccttcact aattacatga tagagtggat aaaacagagg     120
cctggacagg gccttgagtg gattggagtg attaatcctg gaagtggtgg tacttataac     180
agtgagaagg tcaagggcaa ggcaacactg accgcagaca gatcctccag cactgcctac     240
atgcagctca gcagcctgac agctgatgac tctggggtct atttctgtcg gatctatggt     300
aactacaagg ggtactttga ccattggggc caaggcacca ctctcacagt ctcctca        357

<210> SEQ ID NO 8
<211> LENGTH: 363
<212> TYPE: DNA
<213> ORGANISM: Artificial Sequence
<220> FEATURE:
<223> OTHER INFORMATION: 10H7-VH

<400> SEQUENCE: 8
cagatccagt tggtgcagtc tggacctgag ctgaagaagc ctggagagac agtcaagatc      60
tcctgcaagg cttctggtta taccttcaca gactattcaa ttcactgggt gaggcaggct     120
ccaggaaagg gttttaagtg gatgggctgg ataaacactg agactggtga gccaacatat     180
gcagatgact caagggacg gtttgccctc tctttggaaa cctctgccag cactgcctac     240
ttgcagatca acaacctcaa aaatgaggac acggctacat atttctgtgc tagatttgac     300
tacggtacta gttactggta cttcgatgtc tggggcgcag ggaccacggt caccgtctcc     360
tca                                                                    363

<210> SEQ ID NO 9
<211> LENGTH: 351
<212> TYPE: DNA
<213> ORGANISM: Artificial Sequence
<220> FEATURE:
<223> OTHER INFORMATION: 3G8-VH

<400> SEQUENCE: 9
```

-continued

```
cagatccagt tggtgcagtc tggacctgag ctgaagaagc ctggagagac agtcaagatc      60
tcctgcaagg cttctgggta tagcttcaca aagtatggaa tgaactgggt gaagcaggct     120
ccaggaaagg atatcaagtg gatggggtgg ataaacacca acactggaga ggcaacatat     180
ggtgaagagg tcaagggacg gtttgccttc tctttggaaa cctctgccag cactgcctat     240
ttgcagatca acaacctcaa aaatgaggac acggctacat atttctgtgc aagattggga     300
ttgaggtacc ttgactactg gggccaaggc accactctca cagtctcctc a             351
```

<210> SEQ ID NO 10
<211> LENGTH: 336
<212> TYPE: DNA
<213> ORGANISM: Artificial Sequence
<220> FEATURE:
<223> OTHER INFORMATION: 3F12-VH

<400> SEQUENCE: 10

```
caggtgcaac tgcaggagtc aggacctgac ctggtgaaac cttctcagtc actttcactc      60
acctgcactg tcactgggta ctccatcacc agtggttata gctggcactg gatccggcag     120
tttccaggaa acaaattgga atggatgggc tacatatatt atagaggtag cactaactac     180
aacccatctc tcaaaagtcg aatctctatc actcgagaca catccaagaa ccagttcttc     240
ctgctgttga aatctgtgac tactgaggac acagccacat attactgtgc aagagaggct     300
tactggggcc aagggactct ggtcactgtc tcagca                              336
```

<210> SEQ ID NO 11
<211> LENGTH: 336
<212> TYPE: DNA
<213> ORGANISM: Artificial Sequence
<220> FEATURE:
<223> OTHER INFORMATION: 2A11-VL

<400> SEQUENCE: 11

```
gatgttttga tgacccaaac tccactctcc ctgcctgtca gtcttggaga tcaagcctcc      60
atctcttgca gatctagtca gagtattgta catagtaatg gaaacaccta tttagaatgg     120
tacctgcaga agccaggcca gtctccaaag ctcctgatct acaaagtttc caaccgattt     180
tctggggtcc agacaggtt cagtggcagt ggatcaggga cagatttcac actcaagatc      240
agcagagtgg aggctgagga tctgggagtt tatttctgct ttcaaggttc acaggttcct     300
ccgacgttcg gtggaggcac caagctggaa atcaaa                              336
```

<210> SEQ ID NO 12
<211> LENGTH: 336
<212> TYPE: DNA
<213> ORGANISM: Artificial Sequence
<220> FEATURE:
<223> OTHER INFORMATION: 4C2-VL

<400> SEQUENCE: 12

```
gatgttttga tgacccaaac tccactctcc ctgcctgtca gtcttggaga tcaagcctcc      60
atctcttgca gatctagtca gagtattgta catagtaatg gaaacaccta tttagaatgg     120
tacctgcaga agccaggcca gtctccaaag ctcctgttct acaaagtttc caaccgattt     180
tctggggtcc agacaggtt cagtggcagt ggatcaggga cagatttcac actcaagatc      240
agcagagtgg aggctgagga tctgggagtt tatttctgct ttcaaggttc acaggttcct     300
ccgacgttcg gtggaggcac caagctggaa atcaaa                              336
```

<210> SEQ ID NO 13
<211> LENGTH: 336
<212> TYPE: DNA
<213> ORGANISM: Artificial Sequence
<220> FEATURE:
<223> OTHER INFORMATION: 8C4-VL

<400> SEQUENCE: 13

```
gatgttttga tgacccaaac tccactctcc ctgcctgtca gtcttggaga tcaagcctcc      60
atctcttgca gatctagtca gagtattgta catagtaatg gaaacaccta tttagaatgg     120
tacctgcaga agccaggcca gtctccaaag ctcctgttct acaaagtttc caaccgattt     180
tctggggtcc cagacaggtt cagtggcagt ggatcaggga cagatttcac actcaagatc     240
agcagagtgg aggctgagga tctgggagtt tatttctgct ttcaaggttc acaggttcct     300
ccgacgttcg gtggaggcac caagctggaa atcaaa                               336
```

<210> SEQ ID NO 14
<211> LENGTH: 336
<212> TYPE: DNA
<213> ORGANISM: Artificial Sequence
<220> FEATURE:
<223> OTHER INFORMATION: 3B5-VL

<400> SEQUENCE: 14

```
gatgttttga tgacccaaac tccactctcc ctgcctgtca gtcttggaga tcaagcctcc      60
atctcttgca gatccagtca gagccttgta cacagtaatg gaaacaccta tttacattgg     120
tacctgcaga agccaggcca gtctccaaag ctcctgatcc acaaagtttc caaccgattt     180
tctggggtcc cagacaggtt cagtggcagt ggatcaggga cagatttcac actcaagatc     240
agcagagtgg aggctgagga tctgggaatt tatttctgct ctcaaaatac acatattcct     300
ccgacgttcg ctggaggcac caagctggaa atcaaa                               336
```

<210> SEQ ID NO 15
<211> LENGTH: 357
<212> TYPE: DNA
<213> ORGANISM: Artificial Sequence
<220> FEATURE:
<223> OTHER INFORMATION: 9B3-VL

<400> SEQUENCE: 15

```
gaggtccagc tgcaacaatc tggagctgag ctggtaaggc ctgggacttc agtgaaggtg      60
tcctgcaagg cttctggata cgccttcact aattacatga tagagtggat aaaaacagagg    120 cctggacagg gccttgagtg gattggagtg attaatcctg gaagtggtgg tagttattac     180
aatgagaagg tcaagggcaa ggcaacactg accgcagaca aatcctccag cactgcctac     240
atgcagttca gcagcctgac agctgatgac tctgcggtct atttctgtcg gatctatggt     300
aactacaagg ggtactttga ctattggggc caaggcacca ctctcacagt ctcctca        357
```

<210> SEQ ID NO 16
<211> LENGTH: 321
<212> TYPE: DNA
<213> ORGANISM: Artificial Sequence
<220> FEATURE:
<223> OTHER INFORMATION: 9B12-VL

<400> SEQUENCE: 16

```
gacattgtga tgacccagtc tccatcttcc atgtatgcat ctctaggaga gagagtcact      60
atcacttgca aggcgagtca ggacatgaat agctatttaa gctggttcca gcagaaacca     120
```

```
gggaaatctc ctaagaccct gatctatcgt gcaaacagat tggtagatgg ggtcccatca       180
aggttcagtg gcagtggatc tgggcaagat tattctctca ccatcagcag cctggagtat       240
gaagatatgg gaatttatta ttgtctacag aatgatgagt ttccattcac gttcggctcg       300
gggacaaagc tggaaatgaa g                                                  321
```

```
<210> SEQ ID NO 17
<211> LENGTH: 321
<212> TYPE: DNA
<213> ORGANISM: Artificial Sequence
<220> FEATURE:
<223> OTHER INFORMATION: 3B10-VL

<400> SEQUENCE: 17
gacattgtga tgacccagtc tccatcttcc atgtatgcat ctctaggaga gagagtcact        60
atcacttgca aggcgagtca ggacatgaat agctatttaa gctggttcca gcagaaacca       120
gggaaatctc ctaagaccct gatctatcgt tcaaacagat tggtagatgg ggtcccatca       180
aggttcagtg gcagtggatc tgggcaagat tattctctca ccatcagcag cctggactat       240
gaagatatgg gaatttatta ttgtctacag aatgatgagt ttccattcac gttcggctcg       300
gggacaaagc tggaaataaa a                                                  321
```

```
<210> SEQ ID NO 18
<211> LENGTH: 351
<212> TYPE: DNA
<213> ORGANISM: Artificial Sequence
<220> FEATURE:
<223> OTHER INFORMATION: 10H7-VL

<400> SEQUENCE: 18
gatgtccaga tgacccagtc tccatcctcc ctgtctgcat ctgtgggaga cagagccacc        60
atcacttgcc gggcaagtca gagcattagc agctatttaa attggtatca gcagaaaccc       120
gggaaagccc ctaagctcct gatctatgct gcatccagtt tgcaaagtgg ggtcccatca       180
aggttcagtg gcagtggatc tgggacagat ttcactctca ccatcagcag tctgcaacct       240
gaagattttg caacttacta ctgtcaacag agttacacta ccccgctcac tttcggtgga       300
ggcaccaagc tggaaatcaa acgtggagga gccagcctcg tggaattcaa g                351
```

```
<210> SEQ ID NO 19
<211> LENGTH: 333
<212> TYPE: DNA
<213> ORGANISM: Artificial Sequence
<220> FEATURE:
<223> OTHER INFORMATION: 3G8-VL

<400> SEQUENCE: 19
gacattgtga tgacccagtc tcctgcttcc ttagttgtat ctctggggca gagggccacc        60
atctcatgca gggccagcaa aagtgtcagt acatctgact atagttatat gcactggtac       120
caacagaaac caggacagcc acccaaagtc ctcatctatc ttgcatccaa cctagaatct       180
ggggtccctg ccaggttcag tggcagtggg tctgggacag acttcaccct caacatccat       240
cctgtggagg aggaggatgc tgcaacctat tactgtcagc acaataggga gcttcctccc       300
acgttcggtg ctgggaccaa gctggagctg aaa                                    333
```

```
<210> SEQ ID NO 20
<211> LENGTH: 336
<212> TYPE: DNA
<213> ORGANISM: Artificial Sequence
```

<220> FEATURE:
<223> OTHER INFORMATION: 3F12-VL

<400> SEQUENCE: 20

```
gatgttttga tgacccaaac tccactcact ttgtcggtta cctttgggca gccagcctcc       60
atctcttgca ggtcaagtca gagcctctta gatagtgatg gagagacata tttgaattgg      120
ttgttacaga ggccaggcca gtctccaaag cgcctaatct atctggtgtc taaactggac      180
tctggagtcc ctgacaggtt cactggcagt ggatcaggga cagatttcac actgaaaatc      240
agcagagtgg aggctgagga tttgggagtt tattattgct ggcaaggtac acattttccg      300
tacacgttcg gagggggggac caagctggaa ataaaa                                336
```

<210> SEQ ID NO 21
<211> LENGTH: 123
<212> TYPE: PRT
<213> ORGANISM: Artificial Sequence
<220> FEATURE:
<223> OTHER INFORMATION: 2A11,4C2,8C4-VH
<220> FEATURE:
<221> NAME/KEY: VARIANT
<222> LOCATION: (56)..(57)
<223> OTHER INFORMATION: Xaa is Gly or Ala

<400> SEQUENCE: 21

```
Gln Val Gln Leu Gln Gln Pro Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ile Ile Asp Pro Glu Thr Xaa Xaa Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Lys Phe Tyr Tyr Ser Gly Arg Asp Tyr Ala Met Asp Tyr
            100                 105                 110

Trp Gly Gln Gly Thr Ser Val Thr Val Ser Ser
        115                 120
```

<210> SEQ ID NO 22
<211> LENGTH: 122
<212> TYPE: PRT
<213> ORGANISM: Artificial Sequence
<220> FEATURE:
<223> OTHER INFORMATION: 3B5-VH

<400> SEQUENCE: 22

```
Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Ser Phe Thr Asp Tyr
            20                  25                  30

Thr Phe Tyr Trp Val Arg Gln Ser His Gly Glu Ser Leu Glu Trp Ile
        35                  40                  45

Gly Tyr Ile Asp Pro Tyr Asn Gly Gly Asn Thr Tyr Asn Arg Lys Phe
    50                  55                  60

Lys Gly Lys Ala Thr Leu Thr Val Asp Lys Ser Ser Ser Thr Ala Phe
65                  70                  75                  80
```

-continued

```
Met His Leu Asn Ser Leu Thr Ser Glu Asp Ser Ala Val Tyr Tyr Cys
                85                  90                  95

Ala Arg Gly Tyr Tyr Arg Tyr Gly Gly Gly Gly Asp Phe Asp Tyr Trp
            100                 105                 110

Gly Gln Gly Thr Thr Leu Thr Val Ser Ser
        115                 120

<210> SEQ ID NO 23
<211> LENGTH: 119
<212> TYPE: PRT
<213> ORGANISM: Artificial Sequence
<220> FEATURE:
<223> OTHER INFORMATION: 9B3,9B12,3B10-VH
<220> FEATURE:
<221> NAME/KEY: VARIANT
<222> LOCATION: (1)..(1)
<223> OTHER INFORMATION: Xaa is Glu or Gln
<220> FEATURE:
<221> NAME/KEY: VARIANT
<222> LOCATION: (7)..(7)
<223> OTHER INFORMATION: Xaa is Ser or Pro
<220> FEATURE:
<221> NAME/KEY: VARIANT
<222> LOCATION: (12)..(12)
<223> OTHER INFORMATION: Xaa is Val or Ala
<220> FEATURE:
<221> NAME/KEY: VARIANT
<222> LOCATION: (27)..(27)
<223> OTHER INFORMATION: Xaa is Tyr or His
<220> FEATURE:
<221> NAME/KEY: VARIANT
<222> LOCATION: (58)..(58)
<223> OTHER INFORMATION: Xaa is Ser or Thr
<220> FEATURE:
<221> NAME/KEY: VARIANT
<222> LOCATION: (61)..(61)
<223> OTHER INFORMATION: Xaa is Asn or Ser
<220> FEATURE:
<221> NAME/KEY: VARIANT
<222> LOCATION: (74)..(74)
<223> OTHER INFORMATION: Xaa is Arg or Lys
<220> FEATURE:
<221> NAME/KEY: VARIANT
<222> LOCATION: (83)..(83)
<223> OTHER INFORMATION: Xaa is Phe or Leu
<220> FEATURE:
<221> NAME/KEY: VARIANT
<222> LOCATION: (92)..(92)
<223> OTHER INFORMATION: Xaa is Gly or Ala
<220> FEATURE:
<221> NAME/KEY: VARIANT
<222> LOCATION: (108)..(108)
<223> OTHER INFORMATION: Xaa is His or Tyr

<400> SEQUENCE: 23

Xaa Val Gln Leu Gln Gln Xaa Gly Ala Glu Leu Xaa Arg Pro Gly Thr
1               5                   10                  15

Ser Val Lys Val Ser Cys Lys Ala Ser Gly Xaa Ala Phe Thr Asn Tyr
            20                  25                  30

Met Ile Glu Trp Ile Lys Gln Arg Pro Gly Gln Gly Leu Glu Trp Ile
        35                  40                  45

Gly Val Ile Asn Pro Gly Ser Gly Gly Xaa Tyr Tyr Xaa Glu Lys Val
    50                  55                  60

Lys Gly Lys Ala Thr Leu Thr Ala Asp Xaa Ser Ser Ser Thr Ala Tyr
65                  70                  75                  80

Met Gln Xaa Ser Ser Leu Thr Ala Asp Asp Ser Xaa Val Tyr Phe Cys
                85                  90                  95

Arg Ile Tyr Gly Asn Tyr Lys Gly Tyr Phe Asp Xaa Trp Gly Gln Gly
```

-continued

```
              100             105             110

Thr Thr Leu Thr Val Ser Ser
        115

<210> SEQ ID NO 24
<211> LENGTH: 121
<212> TYPE: PRT
<213> ORGANISM: Artificial Sequence
<220> FEATURE:
<223> OTHER INFORMATION: 10H7-VH

<400> SEQUENCE: 24

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile His Trp Val Arg Gln Ala Pro Gly Lys Gly Phe Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Phe Asp Tyr Gly Thr Ser Tyr Trp Tyr Phe Asp Val Trp Gly
            100                 105                 110

Ala Gly Thr Thr Val Thr Val Ser Ser
        115                 120

<210> SEQ ID NO 25
<211> LENGTH: 117
<212> TYPE: PRT
<213> ORGANISM: Artificial Sequence
<220> FEATURE:
<223> OTHER INFORMATION: 3G8-VH

<400> SEQUENCE: 25

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Lys Tyr
            20                  25                  30

Gly Met Asn Trp Val Lys Gln Ala Pro Gly Lys Asp Ile Lys Trp Met
        35                  40                  45

Gly Trp Ile Asn Thr Asn Thr Gly Glu Ala Thr Tyr Gly Glu Glu Val
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Leu Arg Tyr Leu Asp Tyr Trp Gly Gln Gly Thr Thr
            100                 105                 110

Leu Thr Val Ser Ser
        115

<210> SEQ ID NO 26
<211> LENGTH: 112
<212> TYPE: PRT
<213> ORGANISM: Artificial Sequence
<220> FEATURE:
```

-continued

```
<223> OTHER INFORMATION: 3F12-VH

<400> SEQUENCE: 26

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile Tyr Tyr Arg Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Leu Leu Lys Ser Val Thr Thr Glu Asp Thr Ala Thr Tyr Tyr Cys
                85                  90                  95

Ala Arg Glu Ala Tyr Trp Gly Gln Gly Thr Leu Val Thr Val Ser Ala
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: 2A11,4C2,8C4-VL
<220> FEATURE:
<221> NAME/KEY: VARIANT
<222> LOCATION: (53)..(53)
<223> OTHER INFORMATION: Xaa is Ile or Phe

<400> SEQUENCE: 27

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Xaa Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser Gln Val Pro Pro Thr Phe Gly Gly Gly Thr Lys Leu Glu Ile Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: 3B5-VL

<400> SEQUENCE: 28

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

-continued

```
Pro Lys Leu Leu Ile His Lys Val Ser Asn Arg Phe Ser Gly Val Pro
    50              55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Ile Tyr Phe Cys Ser Gln Asn
                85                  90                  95

Thr His Ile Pro Pro Thr Phe Ala Gly Gly Thr Lys Leu Glu Ile Lys
            100                 105                 110
```

<210> SEQ ID NO 29
<211> LENGTH: 107
<212> TYPE: PRT
<213> ORGANISM: Artificial Sequence
<220> FEATURE:
<223> OTHER INFORMATION: 9B3,9B12,3B10-VL
<220> FEATURE:
<221> NAME/KEY: VARIANT
<222> LOCATION: (29)..(29)
<223> OTHER INFORMATION: Xaa is Met or Ile
<220> FEATURE:
<221> NAME/KEY: VARIANT
<222> LOCATION: (51)..(51)
<223> OTHER INFORMATION: Xaa is Ala or Ser
<220> FEATURE:
<221> NAME/KEY: VARIANT
<222> LOCATION: (79)..(79)
<223> OTHER INFORMATION: Xaa is Glu or Asp
<220> FEATURE:
<221> NAME/KEY: VARIANT
<222> LOCATION: (106)..(106)
<223> OTHER INFORMATION: Xaa is Met or Ile

<400> SEQUENCE: 29

```
Asp Ile Val Met Thr Gln Ser Pro Ser Ser Met Tyr Ala Ser Leu Gly
1               5                   10                  15

Glu Arg Val Thr Ile Thr Cys Lys Ala Ser Gln Asp Xaa Asn Ser Tyr
                20                  25                  30

Leu Ser Trp Phe Gln Gln Lys Pro Gly Lys Ser Pro Lys Thr Leu Ile
            35                  40                  45

Tyr Arg Xaa Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Xaa Tyr
65                  70                  75                  80

Glu Asp Met Gly Ile Tyr Tyr Cys Leu Gln Asn Asp Glu Phe Pro Phe
                85                  90                  95

Thr Phe Gly Ser Gly Thr Lys Leu Glu Xaa Lys
            100                 105
```

<210> SEQ ID NO 30
<211> LENGTH: 107
<212> TYPE: PRT
<213> ORGANISM: Artificial Sequence
<220> FEATURE:
<223> OTHER INFORMATION: 10H7-VL

<400> SEQUENCE: 30

```
Asp Val Gln Met Thr Gln Ser Pro Ser Ser Leu Ser Ala Ser Val Gly
1               5                   10                  15

Asp Arg Ala Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
```

```
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Thr Thr Pro Leu
                85              90              95

Thr Phe Gly Gly Gly Thr Lys Leu Glu Ile Lys
            100             105

<210> SEQ ID NO 31
<211> LENGTH: 111
<212> TYPE: PRT
<213> ORGANISM: Artificial Sequence
<220> FEATURE:
<223> OTHER INFORMATION: 3G8-VL

<400> SEQUENCE: 31

Asp Ile Val Met Thr Gln Ser Pro Ala Ser Leu Val Val Ser Leu Gly
1               5               10              15

Gln Arg Ala Thr Ile Ser Cys Arg Ala Ser Lys Ser Val Ser Thr Ser
                20              25              30

Asp Tyr Ser Tyr Met His Trp Tyr Gln Gln Lys Pro Gly Gln Pro Pro
            35              40              45

Lys Val Leu Ile Tyr Leu Ala Ser Asn Leu Glu Ser Gly Val Pro Ala
        50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln His Asn Arg
                85              90              95

Glu Leu Pro Pro Thr Phe Gly Ala Gly Thr Lys Leu Glu Leu Lys
            100             105             110

<210> SEQ ID NO 32
<211> LENGTH: 112
<212> TYPE: PRT
<213> ORGANISM: Artificial Sequence
<220> FEATURE:
<223> OTHER INFORMATION: 3F12-VL

<400> SEQUENCE: 32

Asp Val Leu Met Thr Gln Thr Pro Leu Thr Leu Ser Val Thr Phe Gly
1               5               10              15

Gln Pro Ala Ser Ile Ser Cys Arg Ser Ser Gln Ser Leu Leu Asp Ser
                20              25              30

Asp Gly Glu Thr Tyr Leu Asn Trp Leu Leu Gln Arg Pro Gly Gln Ser
            35              40              45

Pro Lys Arg Leu Ile Tyr Leu Val Ser Lys Leu Asp Ser Gly Val Pro
        50              55              60

Asp Arg Phe Thr Gly Ser Gly Ser Gly Thr Asp Phe Thr Leu Lys Ile
65              70              75              80

Ser Arg Val Glu Ala Glu Asp Leu Gly Val Tyr Tyr Cys Trp Gln Gly
                85              90              95

Thr His Phe Pro Tyr Thr Phe Gly Gly Gly Thr Lys Leu Glu Ile Lys
            100             105             110

<210> SEQ ID NO 33
<211> LENGTH: 8
<212> TYPE: PRT
<213> ORGANISM: Artificial Sequence
<220> FEATURE:
```

<223> OTHER INFORMATION: 2A11,4C2,8C4-VHCDR1

<400> SEQUENCE: 33

Gly Tyr Thr Phe Thr Asp Tyr Glu
1               5

<210> SEQ ID NO 34
<211> LENGTH: 8
<212> TYPE: PRT
<213> ORGANISM: Artificial Sequence
<220> FEATURE:
<223> OTHER INFORMATION: 3B5-VHCDR1

<400> SEQUENCE: 34

Gly Tyr Ser Phe Thr Asp Tyr Thr
1               5

<210> SEQ ID NO 35
<211> LENGTH: 8
<212> TYPE: PRT
<213> ORGANISM: Artificial Sequence
<220> FEATURE:
<223> OTHER INFORMATION: 9B3,9B12,3B10-VHCDR1
<220> FEATURE:
<221> NAME/KEY: VARIANT
<222> LOCATION: (2)..(2)
<223> OTHER INFORMATION: Xaa is Tyr or His

<400> SEQUENCE: 35

Gly Xaa Ala Phe Thr Asn Tyr Met
1               5

<210> SEQ ID NO 36
<211> LENGTH: 8
<212> TYPE: PRT
<213> ORGANISM: Artificial Sequence
<220> FEATURE:
<223> OTHER INFORMATION: 10H7-VHCDR1

<400> SEQUENCE: 36

Gly Tyr Thr Phe Thr Asp Tyr Ser
1               5

<210> SEQ ID NO 37
<211> LENGTH: 8
<212> TYPE: PRT
<213> ORGANISM: Artificial Sequence
<220> FEATURE:
<223> OTHER INFORMATION: 3G8-VHCDR1

<400> SEQUENCE: 37

Gly Tyr Ser Phe Thr Lys Tyr Gly
1               5

<210> SEQ ID NO 38
<211> LENGTH: 9
<212> TYPE: PRT
<213> ORGANISM: Artificial Sequence
<220> FEATURE:
<223> OTHER INFORMATION: 3F12-VHCDR1

<400> SEQUENCE: 38

Gly Tyr Ser Ile Thr Ser Gly Tyr Ser
1               5

<210> SEQ ID NO 39
<211> LENGTH: 8

```
<212> TYPE: PRT
<213> ORGANISM: Artificial Sequence
<220> FEATURE:
<223> OTHER INFORMATION: 2A11,4C2,8C4-VHCDR2
<220> FEATURE:
<221> NAME/KEY: VARIANT
<222> LOCATION: (6)..(7)
<223> OTHER INFORMATION: Xaa is Gly or Ala

<400> SEQUENCE: 39

Ile Asp Pro Glu Thr Xaa Xaa Thr
1               5

<210> SEQ ID NO 40
<211> LENGTH: 8
<212> TYPE: PRT
<213> ORGANISM: Artificial Sequence
<220> FEATURE:
<223> OTHER INFORMATION: 3B5-VHCDR2

<400> SEQUENCE: 40

Ile Asp Pro Tyr Asn Gly Gly Asn
1               5

<210> SEQ ID NO 41
<211> LENGTH: 8
<212> TYPE: PRT
<213> ORGANISM: Artificial Sequence
<220> FEATURE:
<223> OTHER INFORMATION: 9B3,9B12,3B5-VHCDR2
<220> FEATURE:
<221> NAME/KEY: VARIANT
<222> LOCATION: (8)..(8)
<223> OTHER INFORMATION: Xaa is Ser or Thr

<400> SEQUENCE: 41

Ile Asn Pro Gly Ser Gly Gly Xaa
1               5

<210> SEQ ID NO 42
<211> LENGTH: 8
<212> TYPE: PRT
<213> ORGANISM: Artificial Sequence
<220> FEATURE:
<223> OTHER INFORMATION: 10H7-VHCDR2

<400> SEQUENCE: 42

Ile Asn Thr Glu Thr Gly Glu Pro
1               5

<210> SEQ ID NO 43
<211> LENGTH: 8
<212> TYPE: PRT
<213> ORGANISM: Artificial Sequence
<220> FEATURE:
<223> OTHER INFORMATION: 3G8-VHCDR2

<400> SEQUENCE: 43

Ile Asn Thr Asn Thr Gly Glu Ala
1               5

<210> SEQ ID NO 44
<211> LENGTH: 7
<212> TYPE: PRT
<213> ORGANISM: Artificial Sequence
<220> FEATURE:
<223> OTHER INFORMATION: 3F12-VHCDR2

<400> SEQUENCE: 44
```

Ile Tyr Tyr Arg Gly Ser Thr
1               5

<210> SEQ ID NO 45
<211> LENGTH: 16
<212> TYPE: PRT
<213> ORGANISM: Artificial Sequence
<220> FEATURE:
<223> OTHER INFORMATION: 2A11,4C2,8C4-VHCDR3

<400> SEQUENCE: 45

Thr Arg Gly Lys Phe Tyr Tyr Ser Gly Arg Asp Tyr Ala Met Asp Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: 3B5-VHCDR3

<400> SEQUENCE: 46

Ala Arg Gly Tyr Tyr Arg Tyr Gly Gly Gly Gly Asp Phe Asp Tyr
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: 9B3,9B12,3B10-VHCDR3
<220> FEATURE:
<221> NAME/KEY: VARIANT
<222> LOCATION: (12)..(12)
<223> OTHER INFORMATION: Xaa is Tyr or His

<400> SEQUENCE: 47

Arg Ile Tyr Gly Asn Tyr Lys Gly Tyr Phe Asp Xaa
1               5                   10

<210> SEQ ID NO 48
<211> LENGTH: 14
<212> TYPE: PRT
<213> ORGANISM: Artificial Sequence
<220> FEATURE:
<223> OTHER INFORMATION: 10H7-VHCDR3

<400> SEQUENCE: 48

Ala Arg Phe Asp Tyr Gly Thr Ser Tyr Trp Tyr Phe Asp Val
1               5                   10

<210> SEQ ID NO 49
<211> LENGTH: 10
<212> TYPE: PRT
<213> ORGANISM: Artificial Sequence
<220> FEATURE:
<223> OTHER INFORMATION: 3G8-VHCDR3

<400> SEQUENCE: 49

Ala Arg Leu Gly Leu Arg Tyr Leu Asp Tyr
1               5                   10

<210> SEQ ID NO 50
<211> LENGTH: 5
<212> TYPE: PRT
<213> ORGANISM: Artificial Sequence
<220> FEATURE:

<223> OTHER INFORMATION: 3F12-VHCDR3

<400> SEQUENCE: 50

Ala Arg Glu Ala Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: 2A11,4C2,8C4-VLCDR1

<400> SEQUENCE: 51

Gln Ser Ile Val His Ser Asn Gly Asn Thr Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: 3B5-VLCDR1

<400> SEQUENCE: 52

Gln Ser Leu Val His Ser Asn Gly Asn Thr Tyr
1               5                   10

<210> SEQ ID NO 53
<211> LENGTH: 6
<212> TYPE: PRT
<213> ORGANISM: Artificial Sequence
<220> FEATURE:
<223> OTHER INFORMATION: 9B3,9B12,3B10-VLCDR1
<220> FEATURE:
<221> NAME/KEY: VARIANT
<222> LOCATION: (3)..(3)
<223> OTHER INFORMATION: Xaa is Ile or Met

<400> SEQUENCE: 53

Gln Asp Xaa Asn Ser Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: 10H7-VLCDR1

<400> SEQUENCE: 54

Gln Ser Ile Ser Ser Tyr
1               5

<210> SEQ ID NO 55
<211> LENGTH: 10
<212> TYPE: PRT
<213> ORGANISM: Artificial Sequence
<220> FEATURE:
<223> OTHER INFORMATION: 3G8-VLCDR1

<400> SEQUENCE: 55

Lys Ser Val Ser Thr Ser Asp Tyr Ser Tyr
1               5                   10

<210> SEQ ID NO 56
<211> LENGTH: 11

```
<212> TYPE: PRT
<213> ORGANISM: Artificial Sequence
<220> FEATURE:
<223> OTHER INFORMATION: 3F12-VLCDR1

<400> SEQUENCE: 56

Gln Ser Leu Leu Asp Ser Asp Gly Glu Thr Tyr
1               5                   10

<210> SEQ ID NO 57
<211> LENGTH: 3
<212> TYPE: PRT
<213> ORGANISM: Artificial Sequence
<220> FEATURE:
<223> OTHER INFORMATION: 2A11,4C2,8C4-VLCDR2

<400> SEQUENCE: 57

Lys Val Ser
1

<210> SEQ ID NO 58
<211> LENGTH: 3
<212> TYPE: PRT
<213> ORGANISM: Artificial Sequence
<220> FEATURE:
<223> OTHER INFORMATION: 3B5-VLCDR2

<400> SEQUENCE: 58

Lys Val Ser
1

<210> SEQ ID NO 59
<211> LENGTH: 3
<212> TYPE: PRT
<213> ORGANISM: Artificial Sequence
<220> FEATURE:
<223> OTHER INFORMATION: 9B3,9B12,3B10-VLCDR2
<220> FEATURE:
<221> NAME/KEY: VARIANT
<222> LOCATION: (2)..(2)
<223> OTHER INFORMATION: Xaa is Ala or Ser

<400> SEQUENCE: 59

Arg Xaa Asn
1

<210> SEQ ID NO 60
<211> LENGTH: 3
<212> TYPE: PRT
<213> ORGANISM: Artificial Sequence
<220> FEATURE:
<223> OTHER INFORMATION: 10H7-VLCDR2

<400> SEQUENCE: 60

Ala Ala Ser
1

<210> SEQ ID NO 61
<211> LENGTH: 3
<212> TYPE: PRT
<213> ORGANISM: Artificial Sequence
<220> FEATURE:
<223> OTHER INFORMATION: 3G8-VLCDR2

<400> SEQUENCE: 61

Leu Ala Ser
1
```

-continued

```
<210> SEQ ID NO 62
<211> LENGTH: 3
<212> TYPE: PRT
<213> ORGANISM: Artificial Sequence
<220> FEATURE:
<223> OTHER INFORMATION: 3F12-VLCDR2

<400> SEQUENCE: 62

Leu Val Ser
1

<210> SEQ ID NO 63
<211> LENGTH: 9
<212> TYPE: PRT
<213> ORGANISM: Artificial Sequence
<220> FEATURE:
<223> OTHER INFORMATION: 2A11,4C2,8C4-VLCDR3

<400> SEQUENCE: 63

Phe Gln Gly Ser Gln Val Pro Pro Thr
1               5

<210> SEQ ID NO 64
<211> LENGTH: 9
<212> TYPE: PRT
<213> ORGANISM: Artificial Sequence
<220> FEATURE:
<223> OTHER INFORMATION: 3B5-VLCDR3

<400> SEQUENCE: 64

Ser Gln Asn Thr His Ile Pro Pro Thr
1               5

<210> SEQ ID NO 65
<211> LENGTH: 9
<212> TYPE: PRT
<213> ORGANISM: Artificial Sequence
<220> FEATURE:
<223> OTHER INFORMATION: 9B3,9B12,3B10-VLCDR3

<400> SEQUENCE: 65

Leu Gln Asn Asp Glu Phe Pro Phe Thr
1               5

<210> SEQ ID NO 66
<211> LENGTH: 9
<212> TYPE: PRT
<213> ORGANISM: Artificial Sequence
<220> FEATURE:
<223> OTHER INFORMATION: 10H7-VLCDR3

<400> SEQUENCE: 66

Gln Gln Ser Tyr Thr Thr Pro Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: 3G8-VLCDR3

<400> SEQUENCE: 67

Gln His Asn Arg Glu Leu Pro Pro Thr
1               5
```

-continued

```
<210> SEQ ID NO 68
<211> LENGTH: 9
<212> TYPE: PRT
<213> ORGANISM: Artificial Sequence
<220> FEATURE:
<223> OTHER INFORMATION: 3F12-VLCDR3

<400> SEQUENCE: 68

Trp Gln Gly Thr His Phe Pro Tyr Thr
1               5

<210> SEQ ID NO 69
<211> LENGTH: 211
<212> TYPE: PRT
<213> ORGANISM: Homo sapiens

<400> SEQUENCE: 69

Met Ala Gln Ala Lys Ile Asn Ala Lys Ala Asn Glu Gly Arg Phe Cys
1               5                   10                  15

Arg Ser Ser Ser Met Ala Asp Arg Ser Ser Arg Leu Leu Glu Ser Leu
                20                  25                  30

Asp Gln Leu Glu Leu Arg Val Glu Ala Leu Arg Glu Ala Ala Thr Ala
            35                  40                  45

Val Glu Gln Glu Lys Glu Ile Leu Leu Glu Met Ile His Ser Ile Gln
        50                  55                  60

Asn Ser Gln Asp Met Arg Gln Ile Ser Asp Gly Glu Arg Glu Glu Leu
65                  70                  75                  80

Asn Leu Thr Ala Asn Arg Leu Met Gly Arg Thr Leu Thr Val Glu Val
                85                  90                  95

Ser Val Glu Thr Ile Arg Asn Pro Gln Gln Gln Glu Ser Leu Lys His
                100                 105                 110

Ala Thr Arg Ile Ile Asp Glu Val Val Asn Lys Phe Leu Asp Asp Leu
                115                 120                 125

Gly Asn Ala Lys Ser His Leu Met Ser Leu Tyr Ser Ala Cys Ser Ser
        130                 135                 140

Glu Val Pro His Gly Pro Val Asp Gln Lys Phe Gln Ser Ile Val Ile
145                 150                 155                 160

Gly Cys Ala Leu Glu Asp Gln Lys Lys Ile Lys Arg Arg Leu Glu Thr
                165                 170                 175

Leu Leu Arg Asn Ile Glu Asn Ser Asp Lys Ala Ile Lys Leu Leu Glu
                180                 185                 190

His Ser Lys Gly Ala Gly Ser Lys Thr Leu Gln Gln Asn Ala Glu Ser
        195                 200                 205

Arg Phe Asn
    210

<210> SEQ ID NO 70
<211> LENGTH: 636
<212> TYPE: DNA
<213> ORGANISM: Homo sapiens

<400> SEQUENCE: 70
atggctcagg cgaagatcaa cgctaaagcc aacgagggc gcttctgccg ctcctcctcc      60
atggctgacc gctccagccg cctgctggag agcctggacc agctggagct cagggttgaa     120
gctttgagag aagcagcaac tgctgttgag caagagaaag aaatccttct ggaaatgatc     180
cacagtatcc aaaatagcca ggacatgagg cagatcagtg acggagaaag agaagaatta     240
aatctgactg caaaccgttt gatgggaaga actctcaccg ttgaagtgtc agtagaaaca     300
```
attagaaacc cccagcagca agaatccta aagcatgcca caaggattat tgatgaggtg          360
gtcaataagt ttctggatga tttgggaaat gccaagagtc atttaatgtc gctctacagt          420
gcatgttcat ctgaggtgcc acatgggcca gttgatcaga agtttcaatc catagtaatt          480
ggctgtgctc ttgaagatca gaagaaaatt aagagaagat tagagactct gcttagaaat          540
attgaaaact ctgacaaggc catcaagcta ttagagcatt ctaaaggagc tggttccaaa          600
actctgcaac aaaatgctga aagcagattc aattag                                    636

<210> SEQ ID NO 71
<211> LENGTH: 270
<212> TYPE: DNA
<213> ORGANISM: Artificial Sequence
<220> FEATURE:
<223> OTHER INFORMATION: GST-Bag F1 vector

<400> SEQUENCE: 71
atggctcagg cgaagatcaa cgctaaagcc aacgaggggc gcttctgccg ctcctcctcc           60
atggctgacc gctccagccg cctgctggag agcctggacc agctggagct cagggttgaa          120
gctttgagag aagcagcaac tgctgttgag caagagaaag aaatccttct ggaaatgatc          180
cacagtatcc aaaatagcca ggacatgagg cagatcagtg acggagaaag agaagaatta          240
aatctgactg caaaccgttt gatgggaaga                                            270

<210> SEQ ID NO 72
<211> LENGTH: 360
<212> TYPE: DNA
<213> ORGANISM: Artificial Sequence
<220> FEATURE:
<223> OTHER INFORMATION: GST-Bag F2 vector

<400> SEQUENCE: 72
atggctcagg cgaagatcaa cgctaaagcc aacgaggggc gcttctgccg ctcctcctcc           60
atggctgacc gctccagccg cctgctggag agcctggacc agctggagct cagggttgaa          120
gctttgagag aagcagcaac tgctgttgag caagagaaag aaatccttct ggaaatgatc          180
cacagtatcc aaaatagcca ggacatgagg cagatcagtg acggagaaag agaagaatta          240
aatctgactg caaaccgttt gatgggaaga actctcaccg ttgaagtgtc agtagaaaca          300
attagaaacc cccagcagca agaatccta aagcatgcca caaggattat tgatgaggtg          360

<210> SEQ ID NO 73
<211> LENGTH: 450
<212> TYPE: DNA
<213> ORGANISM: Artificial Sequence
<220> FEATURE:
<223> OTHER INFORMATION: GST-Bag F3 vector

<400> SEQUENCE: 73
atggctcagg cgaagatcaa cgctaaagcc aacgaggggc gcttctgccg ctcctcctcc           60
atggctgacc gctccagccg cctgctggag agcctggacc agctggagct cagggttgaa          120
gctttgagag aagcagcaac tgctgttgag caagagaaag aaatccttct ggaaatgatc          180
cacagtatcc aaaatagcca ggacatgagg cagatcagtg acggagaaag agaagaatta          240
aatctgactg caaaccgttt gatgggaaga actctcaccg ttgaagtgtc agtagaaaca          300
attagaaacc cccagcagca agaatccta aagcatgcca caaggattat tgatgaggtg          360
gtcaataagt ttctggatga tttgggaaat gccaagagtc atttaatgtc gctctacagt          420

-continued

```
gcatgttcat ctgaggtgcc acatgggcca                              450

<210> SEQ ID NO 74
<211> LENGTH: 540
<212> TYPE: DNA
<213> ORGANISM: Artificial Sequence
<220> FEATURE:
<223> OTHER INFORMATION: GST-Bag F4 vector

<400> SEQUENCE: 74
atggctcagg cgaagatcaa cgctaaagcc aacgaggggc gcttctgccg ctcctcctcc     60
atggctgacc gctccagccg cctgctggag agcctggacc agctggagct cagggttgaa    120
gctttgagag aagcagcaac tgctgttgag caagagaaag aaatccttct ggaaatgatc    180
cacagtatcc aaaatagcca ggacatgagg cagatcagtg acggagaaag agaagaatta    240
aatctgactg caaaccgttt gatgggaaga actctcaccg ttgaagtgtc agtagaaaca    300
attagaaacc cccagcagca agaatcccta aagcatgcca caaggattat tgatgaggtg    360
gtcaataagt ttctggatga tttgggaaat gccaagagtc atttaatgtc gctctacagt    420
gcatgttcat ctgaggtgcc acatgggcca gttgatcaga agtttcaatc catagtaatt    480
ggctgtgctc ttgaagatca gaagaaaatt aagagaagat tagagactct gcttagaaat    540
```

METHODS FOR DIAGNOSING CANCER USING ANTI-BAG2 ANTIBODY

This application is the U.S. national phase of International Application No. PCT/IB2020/051139 filed Feb. 12, 2020 which designated the U.S. and claims priority to Korean Patent Application Nos. 10-2019-0016347 filed Feb. 12, 2019, and 10-2019-0016359 filed Feb. 12, 2019, the entire contents of each of which are hereby incorporated by reference.

The specification further incorporates by reference the Sequence Listing submitted on Feb. 16, 2021. The Sequence Listing.txt file, identified as 6987_0410_Substitute_Sequence_Listing, is 38,609 bytes in size and was created on Feb. 13, 2021. The Sequence Listing, electronically filed, does not extend beyond the scope of the specification, and does not contain new matter.

BACKGROUND OF THE INVENTION

1. Field of the Invention

The present disclosure relates to a composition for use in diagnosing cancer including an antibody or antigen-binding fragment thereof that specifically binds to a BAG2 polypeptide or fragment thereof and a method of providing information used for diagnosing cancer.

2. General Background and State of the Art

The co-chaperone Bcl-2-associated athanogene (BAG) protein family mediates a variety of physiological processes, including intracellular protein folding, stress response, neuronal differentiation, apoptosis, and cell proliferation, and functionally binds to various cooperative proteins. BAG2, one of the members of the BAG domain family with anti-apoptosis activity, is a negative regulator of the C-terminus of Hsc70-interacting protein (CHIP), which is a chaperone-associated ubiquitin ligase. The main role of BAG2 in the regulation of proteins through inhibiting CHIP activity is associated with neurodegenerative diseases and autosomal recessive disorders through the stabilization of chaperone related proteins such as PINK1 and CFTR. It is reported that BAG2 has a pro-apoptotic activity in such a way that expression of BAG2 increases proteasome inhibitor-induced apoptosis, and BAG2 knockdown partially inhibits apoptosis when thyroid carcinoma cells are exposed to proteasome inhibitor MG132. It is also reported that, in various mutant K-Ras-induced tumors, overexpression of BAG2 promotes the stabilization of STK33 protein, which is a potent tumor gene, and thus promotes the development of tumor. However, despite these findings, the role of BAG2 in the progression and metastasis of cancer is not clearly known.

Accordingly, there is a need to develop compositions and methods for diagnosing cancer using antibodies that specifically bind to a BAG2 polypeptide or fragment thereof.

SUMMARY OF THE INVENTION

These and other objects of the invention will be more fully understood from the following description of the invention, the referenced drawings attached hereto and the claims appended hereto.

One aspect provides a composition for use in diagnosing cancer including an antibody or antigen-binding fragment thereof that specifically binds to a BAG2 polypeptide or fragment thereof.

Another aspect provides a kit for use in diagnosing cancer including the composition.

Another aspect provides a method of providing information used for diagnosing cancer.

Additional aspects will be set forth in part in the description which follows and, in part, will be apparent from the description, or may be learned by practice of the presented embodiments of the disclosure.

One aspect provides a composition for use in diagnosing cancer including an antibody or antigen-binding fragment thereof that specifically binds to a BAG2 polypeptide or fragment thereof.

BAG2 polypeptides may be derived from a mammal. The mammal may be a human (*Homo sapiens*), a mouse (Mus muscu/us), a monkey, cow, or a horse. BAG2 may include the amino acid sequence of SEQ ID NO: 69. The amino acid sequence of SEQ ID NO: 69 is a sequence corresponding to NCBI Reference SEQ ID NO: NM_004282.4. The BAG2 protein includes variants which have biologically equivalent activity to the amino acid sequence of SEQ ID NO: 69 although their amino acid sequences do not match the amino acid sequence of SEQ ID NO: 69. The BAG2 polypeptide may include an amino acid sequence having at least 60%, for example, at least 70%, at least 80%, at least 90%, at least 95%, at least 99%, or 100% sequence identity with the sequence of SEQ ID NO: 69. The BAG2 protein may be a polypeptide having the same sequence of SEQ ID NO: 69 except for at least one amino acid residue, at least two amino acid residues, at least three amino acid residues, at least four amino acid residues, at least five amino acid residues, at least six amino acid residues, or at least seven amino acid residue residues. In the present specification, the 'polypeptide' may be used interchangeably with the 'protein'.

The antibody refers to a specific immunoglobulin directed against an antigenic site. The antibody refers to a polypeptide or a combination of polypeptides that specifically binds to a BAG2 polypeptide or fragment thereof. The antibody includes polyclonal antibodies, monoclonal antibodies, or recombinant antibodies, such as ScFv fragments, diabodies, single chain antibodies, and the like, and include all immunoglobulin antibodies. The antibody may include a full form of antibody having two full-length light chains and two full-length heavy chains and may also include functional fragments of antibody molecules thereof that retain antigen-binding function due to the inclusion of having specific antigen-binding sites, that is, binding domains despite the absence of the structure of a full form intact antibody with two light chains and two heavy chains.

The antigen-binding fragment is a fragment of the entire structure of the immunoglobulin, and refers to a portion of the polypeptide including a portion to which an antigen is able to bind. For example, the antigen-binding fragment may be scFv, (scFv)2, Fv, Fab, Fab', Fv F(ab')2, or a combination thereof.

There are five kinds of heavy chains γ, δ, α, μ and ε and a heavy chain may determine the type of antibody. α and γ each include 450 amino acids and μ and ε each include 550 amino acids. The heavy chain has two regions, that is, a variable region and a constant region.

There are two kinds of light chains kappa and lambda and may include about 211 amino acids to about 217 amino acids. A light chain may have a constant region and a variable region.

The antibody or antigen-binding fragment thereof may include a heavy chain variable region including a complementarity determining region (VH-CDR)1 consisting of the amino acid sequence of SEQ ID NO: 33, a VH-CDR2 consisting of the amino acid sequence of SEQ ID NO: 39, and a VH-CDR3 consisting of the amino acid sequence of SEQ ID NO: 45, and a light chain variable region including a complementarity determining region (VL-CDR)1 consisting of the amino acid sequence of SEQ ID NO: 51, a VL-CDR2 consisting of the amino acid sequence of SEQ ID NO: 57, and a VL-CDR3 consisting of the amino acid sequence of SEQ ID NO: 63;

a heavy chain variable region including a VH-CDR1 consisting of the amino acid sequence of SEQ ID NO: 34, a VH-CDR2 consisting of the amino acid sequence of SEQ ID NO: 40, and a VH-CDR3 consisting of the amino acid sequence of SEQ ID NO: 46, and a light chain variable region including a VL-CDR1 consisting of the amino acid sequence of SEQ ID NO: 52, a VL-CDR2 consisting of the amino acid sequence of SEQ ID NO: 58, and a VL-CDR3 consisting of the amino acid sequence of SEQ ID NO: 64;

a heavy chain variable region including a VH-CDR1 consisting of the amino acid sequence of SEQ ID NO: 35, a VH-CDR2 consisting of the amino acid sequence of SEQ ID NO: 41, and a VH-CDR3 consisting of the amino acid sequence of SEQ ID NO: 47, and a light chain variable region including a VL-CDR1 consisting of the amino acid sequence of SEQ ID NO: 53, a VL-CDR2 consisting of the amino acid sequence of SEQ ID NO: 59, and a VL-CDR3 consisting of the amino acid sequence of SEQ ID NO: 65;

a heavy chain variable region including a VH-CDR1 consisting of the amino acid sequence of SEQ ID NO: 36, a VH-CDR2 consisting of the amino acid sequence of SEQ ID NO: 42, and a VH-CDR3 consisting of the amino acid sequence of SEQ ID NO: 48, and a light chain variable region including a VL-CDR1 consisting of the amino acid sequence of SEQ ID NO: 54, a VL-CDR2 consisting of the amino acid sequence of SEQ ID NO: 60, and a VL-CDR3 consisting of amino acid sequence of SEQ ID NO: 66;

a heavy chain variable region including a VH-CDR1 consisting of the amino acid sequence of SEQ ID NO: 37, a VH-CDR2 consisting of the amino acid sequence of SEQ ID NO: 43, and a VH-CDR3 consisting of the amino acid sequence of SEQ ID NO: 49, and a light chain variable region including a VL-CDR1 consisting of the amino acid sequence of SEQ ID NO: 55, a VL-CDR2 consisting of the amino acid sequence of SEQ ID NO: 61, and a VL-CDR3 consisting of the amino acid sequence of SEQ ID NO: 67; and a heavy chain variable region including a VH-CDR1 consisting of the amino acid sequence of SEQ ID NO: 38, a VH-CDR2 consisting of the amino acid sequence of SEQ ID NO: 44, and a VH-CDR3 consisting of the amino acid sequence of SEQ ID NO: 50, and a light chain variable region including a VL-CDR1 consisting of the amino acid sequence of SEQ ID NO: 56, a
VL-CDR2 consisting of the amino acid sequence of SEQ ID NO: 62, and a VL-CDR3 consisting of the amino acid sequence of SEQ ID NO: 68; or a combination thereof.

The 6th and 7th Xaa in SEQ ID NO: 39 may be glycine (Gly) or alanine (Ala). The 2nd Xaa in SEQ ID NO: 35 may be tyrosine (Tyr) or histidine (His). The 8th Xaa in SEQ ID NO: 41 may be serine (Ser) or threonine (Thr). The 12th Xaa in SEQ ID NO: 47 may be tyrosine (Tyr) or histidine (His). The 3rd Xaa in SEQ ID NO: 53 may be methionine (Met) or isoleucine (lie). The 2nd Xaa in SEQ ID NO: 59 may be Ala or Ser.

The antibody or antigen-binding fragment thereof may be an antibody or antigen-binding fragment thereof, including a heavy chain variable region including a VH-CDR1 consisting of amino acid sequence of SEQ ID NO: 33, a VH-CDR2 consisting of the amino acid sequence of SEQ ID NO: 39 wherein 6th and 7th Xaa are Gly, and a VH-CDR3 consisting of the amino acid sequence of SEQ ID NO: 45, and a light chain variable region including a VL-CDR1 consisting of the amino acid sequence of SEQ ID NO: 51, a VL-CDR2 consisting of the amino acid sequence of SEQ ID NO: 57, and a VL-CDR3 consisting of the amino acid sequence of SEQ ID NO: 63; or an antibody or antigen-binding fragment thereof, including a heavy chain variable region including a VH-CDR1 consisting of the amino acid sequence of SEQ ID NO: 38, a VH-CDR2 consisting of the amino acid sequence of SEQ ID NO: 44, and a VH-CDR3 consisting of the amino acid sequence of SEQ ID NO: 50 and a light chain variable region including a VL-CDR1 consisting of the amino acid sequence of SEQ ID NO: 56, a VL-CDR2 consisting of the amino acid sequence of SEQ ID NO: 62, and a VL-CDR3 consisting of the amino acid sequence of SEQ ID NO: 68.

The antibody or antigen-binding fragment thereof may be an antibody or antigen-binding fragment thereof, including a heavy chain variable region including a VH-CDR1 consisting of the amino acid sequence of SEQ ID NO: 35 in which the 2nd Xaa is Tyr, a VH-CDR2 consisting of the amino acid sequence of SEQ ID NO: 41 in which the 8th Xaa is Ser, and a VH-CDR3 consisting of the amino acid sequence of SEQ ID NO: 47 in which the 12th Xaa is His, and a light chain variable region including a VL-CDR1 consisting of the amino acid sequence of SEQ ID NO: 53 in which the 3rd Xaa is Met, a VL-CDR2 consisting of the amino acid sequence of SEQ ID NO: 59 wherein the 2nd Xaa is Ala, and a VL-CDR3 consisting of the amino acid sequence of SEQ ID NO: 65; or an antibody or antigen-binding fragment thereof, including a heavy chain variable region including a VH-CDR1 consisting of the amino acid sequence of SEQ ID NO: 37, a VH-CDR2 consisting of the amino acid sequence of SEQ ID NO: 43, and a VH-CDR3 consisting of the amino acid sequence of SEQ ID NO: 49, and a light chain variable region including a VL-CDR1 consisting of the amino acid sequence of SEQ ID NO: 55, a VL-CDR2 consisting of the amino acid sequence of SEQ ID NO: 61, and a VL-CDR3 consisting of the amino acid sequence of SEQ ID NO: 67.

The antibody or antigen-binding fragment thereof may be a antibody or antigen-binding fragment thereof, including a heavy chain variable region including a VH-CDR1 consisting of amino acid sequence of SEQ ID NO: 33, a VH-CDR2 consisting of the amino acid sequence of SEQ ID NO: 39 wherein 6th Xaa and 7th Xaa are Ala and Gly, respectively, and a VH-CDR3 consisting of the amino acid sequence of SEQ ID NO: 45, and a light chain variable region including a VL-CDR1 consisting of the amino acid sequence of SEQ ID NO: 51, a VL-CDR2 consisting of the amino acid sequence of SEQ ID NO: 57, and a VL-CDR3 consisting of the amino acid sequence of SEQ ID NO: 63; or an antibody or antigen-binding fragment thereof, including a heavy chain variable region including a VH-CDR1 consisting of the amino acid sequence of SEQ ID NO: 37, a VH-CDR2 consisting of the amino acid sequence of SEQ ID NO: 43, and a VH-CDR3 consisting of the amino acid sequence of SEQ ID NO: 49 and a light chain variable region including a VL-CDR1 consisting of the amino acid sequence of SEQ ID NO: 55, a VL-CDR2 consisting of the amino acid sequence of SEQ ID NO: 61, and a VL-CDR3 consisting of the amino acid sequence of SEQ ID NO: 67.

The antibody or antigen-binding fragment thereof may be an antibody or antigen-binding fragment thereof, including a heavy chain variable region including a VH-CDR1 consisting of the amino acid sequence of SEQ ID NO: 36, a VH-CDR2 consisting of the amino acid sequence of SEQ ID NO: 44, and a VH-CDR3 consisting of the amino acid sequence of SEQ ID NO: 50 and a light chain variable region including a VL-CDR1 consisting of the amino acid sequence of SEQ ID NO: 56, a VL-CDR2 consisting of the amino acid sequence of SEQ ID NO: 62, and a VL-CDR3 consisting of the amino acid sequence of SEQ ID NO: 68; or an antibody or antigen-binding fragment thereof, including a heavy chain variable region including a VH-CDR1 consisting of the amino acid sequence of SEQ ID NO: 37, a VH-CDR2 consisting of the amino acid sequence of SEQ ID NO: 43, and a VH-CDR3 consisting of the amino acid sequence of SEQ ID NO: 49, and a light chain variable region including a VL-CDR1 consisting of the amino acid sequence of SEQ ID NO: 55, a VL-CDR2 consisting of the amino acid sequence of SEQ ID NO: 61, and a VL-CDR3 consisting of the amino acid sequence of SEQ ID NO: 67.

The antibody or antigen-binding fragment thereof may include a heavy chain variable region including an amino acid sequence of any one selected from SEQ ID NOS: 21 to 26; a light chain variable region including an amino acid sequence of any one selected from SEQ ID NOS: 27 to 32; or the heavy chain variable region and the light chain variable region.

The antibody or antigen-binding fragment thereof may include a heavy chain variable region of SEQ ID NO: 21 and a light chain variable region of SEQ ID NO: 27; a heavy chain variable region of SEQ ID NO: 22 and a light chain variable region of SEQ ID NO: 28; a heavy chain variable region of SEQ ID NO: 23 and a light chain variable region of SEQ ID NO: 29; a heavy chain variable region of SEQ ID NO: 24 and a light chain variable region of SEQ ID NO: 30; a heavy chain variable region of SEQ ID NO: 25 and a light chain variable region of SEQ ID NO: 31; or a heavy chain variable region of SEQ ID NO: 26 and a light chain variable region of SEQ ID NO: 32, or a combination thereof.

The 56th and 57th Xaa in SEQ ID NO: 21 may be Gly or Ala. In SEQ ID NO: 23, the 1st Xaa may be glutamine (Gln) or glutamate (Glu), the 7th Xaa may be Ser or proline (Pro), the 12th Xaa may be valine (Val) or alanine(Ala), the 27th Xaa may be Tyr or His, the 58th Xaa may be Ser or Thr, the 61st Xaa may be asparagine (Asn) or Ser, the 74 th Xaa may be arginine (Arg) or lysine (Lys), the 83rd Xaa may be phenylalanine (Phe) or leucine (Leu), the 92nd Xaa may be Gly or Ala, and the 108th Xaa may be His or Tyr. The 53rd Xaa in SEQ ID NO: 27 may be Ile or Phe. In SEQ ID NO: 29, the 29th Xaa may be Met or Ile, the 51st Xaa may be Ala or Ser, and the 79th Xaa may be Glu or aspartic acid (Asp), and the 106th Xaa may be Met or Ile.

The antibody or antigen-binding fragments thereof may be a monoclonal antibody.

The antibody or antigen-binding fragments thereof may be marked with a detectable label or a label capable of emitting a detectable signal. The label refers to a detectable compound or composition conjugated directly or indirectly to an antibody to produce a labeled antibody or antigen-binding fragment thereof. The label may be detectable by itself and catalyze the chemical modification of the detectable substrate compound or composition. The label may be an immunofluorescent label, a chemiluminescent label, a phosphorescent label, a radiolabel, an epitope tag, avidin/ biotin, colloidal gold particles, colored particles, magnetic particles, chromophore labels, an ECL label, an enzyme, or the like.

The antibody or antigen-binding fragment thereof may be produced by a hybridoma cell selected from hybridoma cells deposited with accession numbers KCTC 137378P, KCTC 137388P, KCTC 137398P, KCTC 137408P, KCTC 137418P, KCTC 137428P, KCTC 137438P, KCTC 137448P, KCTC 137458P and KCTC 137468P.

The hybridoma cell refers to a hybrid cell having tumorigenicity by artificial fusion of two kinds of cells, and in general, may be used to continuously produce antibodies by fusing B cells and plasmacytoma cells isolated from an immunized subject. In the present specification, the hybridoma cells may be referred to as hybridoma cells or fusion cells.

The cancer may be solid or non-solid cancer. Solid cancer refers to the development of cancerous tumors in organs such as the liver, lungs, breasts and the skin. Non-solid cancers are cancers that occur in the blood and are also called hematologic cancers. The cancer may be carcinoma, sarcoma, cancer derived from hematopoietic cells, germ cell tumor, or blastoma. The cancer may be selected from, for example, breast cancer, colorectal cancer, head and neck cancer, colon cancer, skin cancer, pancreatic cancer, lung cancer, gastric cancer, prostate cancer, bladder cancer, urethral cancer, liver cancer, kidney cancer, clear cell sarcoma, melanoma, cerebrospinal tumor, brain cancer, thymus, mesothelioma, esophageal cancer, bile duct cancer, testicular cancer, germ cell tumor, thyroid cancer, parathyroid cancer, cervical cancer, endometrial cancer, lymphoma, myelodysplastic syndromes (MOS), myelofibrosis, acute leukemia, chronic leukemia, multiple myeloma, Hodgkin's disease, endocrine cancer, and sarcoma.

The inventors found that, when an anti-BAG2 antibody or antigen-binding fragment thereof, in particular, a combination of the anti-BAG2 antibody or antigen-binding fragment thereof selected by BAG2 domain screening is used, the presence of BAG2 was identified or the level thereof was markedly high in cancer cell lines including breast cancer cell lines, pancreatic cancer cell lines, glioblastoma multiforme cell line, gastric cancer cell line, ovarian cancer cell line, or diffuse large B-cell lymphoma cell line, unlike in normal cells. Thus, the cancer that is be diagnosed by using the composition may be selected from breast cancer, pancreatic cancer, glioma, gastric cancer, ovarian cancer, and lymphoma.

The inventors found that, when an anti-BAG2 antibody or antigen-binding fragment thereof, and in particular, the combination of an anti-BAG2 antibody or antigen-binding fragment thereof is used, BAG2 is overexpressed in breast cancer patients compared to normal subjects, and when levels of BAG2 are high, breast cancer patients have a high probability of having metastatic breast cancer. Thus, the breast cancer diagnosed with the composition may be metastatic breast cancer.

Among the molecular subtypes of breast cancer, triple-negative breast cancer (TNBC) is of a very aggressive type with poor prognosis and high mortality despite a systematic treatment. TNBC is of a heterogeneous type compared to the luminal type or the HER2-enriched type. While most targeted breast cancer therapies have shown positive outcomes against hormonal receptors and HER2-positive breast cancers, since TNBC patients lack three types of target receptors including estrogen receptor (ER), progesterone receptor (PR), human epidermal growth factor receptor (HER2), or other well-defined molecular targets, there is a need to include limited options for effective treatment, for example, poly ADP-ribose polymerase (PARP), epidermal growth factor receptor (EGFR), Src tyrosine kinase, or the like. Therefore, in order to prevent unnecessary therapeutic approaches and to select effective treatments for TNBC patients, there is a need to quickly and accurately distinguish TNBC patients from various types of breast cancer patients.

The inventors found that, when an anti-BAG2 antibody or antigen-binding fragment thereof, and in particular, the combination of an anti-BAG2 antibody or antigen-binding fragment thereof is used, BAG2 is overexpressed in breast cancer patients, and when levels of BAG2 are high, breast cancer patients has a high probability of diagnosing TNBC type breast cancer. Thus, breast cancer that can be diagnosed by using the method may be triple negative breast cancer or TNBC type breast cancer.

Another aspect provides a kit for use in diagnosing cancer including the composition.

The kit may further include one or more other component compositions, solutions, or devices, which are suitable for an analytical method used by the kit, for example, Western blotting, ELISA, radioimmunoassay, radioimmunodiffusion, ouchterlony immunodiffusion, rocket immunoelectrophoresis, tissue immunostaining, immunoprecipitation assay, complement fixation method, FAGS, protein chips, or a combination thereof. For example, for the detection of immune complexes of BAG2 in samples with antibodies specific to each of them, the kit may further include a substrate, a suitable buffer, a secondary antibody marked with a coloring enzyme or a fluorescent substance, or a coloring substrate. The substrate may be a nitrocellulose membrane, a 96 well plate synthesized with polyvinyl resin, a 96 well plate synthesized with polystyrene resin, a glass slide glass, or the like; the coloring enzyme may be peroxidase, alkaline phosphatase, or the like; the fluorescent substance may be fluorescein isothiocyanate (FITC), rhodamine B-isothiocyanate (RITC), or the like; and the coloring substrate may be 2,2'-azino-bis(3-ethylbenzothiazoline-6-sulphonic acid) (ABTS), o-penylenediamine (OPD), tetramethylbenzidine (TMB), or the like.

Another aspect provides a method of providing information used for diagnosing cancer.

The method is a method of providing information used to diagnose cancer, wherein the presence of BAG2 in a subject is detected to diagnose cancer present in the subject.

The method may include contacting a sample isolated from a subject with an antibody that specifically binds to a BAG2 polypeptide or fragment thereof; and measuring a formed complex of the BAG2 polypeptide or fragment thereof and the antibody.

The method may further include determining whether the subject has cancer. The information may be information about whether the level of the BAG2 measured in the subject is higher, the same or lower than the level of the BAG2 measured in the control group.

The sample may be a biological sample as separated from a subject to be diagnosed. The biological sample may be cells, organs, cell lysates, whole blood, blood, serum, plasma, lymphatic fluid, extracellular fluid, body fluids, urine, feces, tissues, bone marrow, saliva, sputum, cerebrospinal fluids, or a combination thereof.

The sample may be blood, serum, plasma, or a combination thereof. The inventors have demonstrated that BAG2 is secreted out of cells and that BAG2 is actually be detected by using the anti-BAG2 antibody or antigen-binding fragments thereof in the serum of breast cancer patients. Therefore, BAG2 may be soluble in blood, serum, plasma, or a combination thereof.

When BAG2 is present in a sample isolated from a subject, an antibody that specifically binds to a BAG2 polypeptide or fragment thereof may bind to BAG2 in the sample. The antibody may be labeled with, for example, fluorophore, chromopore, or an enzyme capable of converting a substrate into a chromophore, for example, to visualize the presence of BAG2 in the sample.

Due to the binding reaction, BAG2 in the sample forms a complex with the antibody that specifically binds to the BAG2 polypeptide or a fragment thereof, and, from the complex, the presence of BAG2 or the level thereof, if needed, may be identified or measured by using a method known to those skilled in the art. The complex may be measured by Western blotting, enzyme linked immunosorbent assay (ELISA), radioimmunoassay (RIA), radioimmunodiffusion, ouchterlony immunodiffusion, rocket immunoelectrophoresis, tissue immunostaining, immunoprecipitation assay, complement fixation assay, FACS, protein chip, or a combination thereof. The measurement may be performed to measure the level of the complex in the sample.

The control group may be a sample taken from a healthy subject or a sample taken from breast cancer, pancreatic cancer, glioblastoma multiforme, gastric cancer, ovarian cancer, or diffuse large B-cell lymphoma (DLBCL). Accordingly, the BAG2 level of the control group may be an average value of the concentration of BAG2 in a sample taken from a healthy subject or, if needed, a sample taken from breast cancer, pancreatic cancer, glioblastoma multiforme, gastric cancer, ovarian cancer, or DLBCL patients.

The sample used as the control may be of the same kind as taken at the same location anatomically as the sample for diagnosis. For example, when the sample is blood collected from the median cubital vein of the subject, the control may also be blood collected from the medial palatine vein of the control group.

The healthy subject is a subject that does not suffer from any acute or chronic disease, at least cancer, for example, breast cancer, pancreatic cancer, glioblastoma multiforme, gastric cancer, ovarian cancer, or DLBCL.

The BAG2 level in the sample collected from the healthy subject may be substantially free of BAG2. Therefore, in the case in which the control group is set to have a value obtained from a healthy subject, when a subject to be diagnosed is found to have BAG2, or the level of BAG2 therein is markedly high, the subject may be suspected of having cancer. On the other hand, as shown in section 3 of Example 2 of the present specification, in the blood of metastatic breast cancer patients, for example, TNBC type patients among breast cancer patients, there is a high probability to identify the presence of BAG2 and the average value of BAG2 is significantly high (FIGS. 7 and 8). Therefore, in the case in which the control group is set to a sample isolated from a breast cancer patient, a non-metastatic breast cancer patient or a non-TNBC type breast cancer patient, when the level of BAG2 is determined to be significantly high in a subject to be diagnosed, the subject may be suspected of having that you have metastatic breast cancer or TNBC type breast cancer.

Therefore, in one aspect, the invention is directed to a method for detecting presence of cancer in an individual comprising contacting a biological sample isolated from the individual with an antibody or antigen-binding fragment thereof that specifically binds to a BAG2 polypeptide or fragment thereof; and measuring a formed complex of the BAG2 polypeptide or fragment thereof and the antibody or antigen-binding fragment thereof, wherein if the BAG2 measured in the sample is higher, than the level of the BAG2 measured in a negative control group the presence of cancer is detected.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
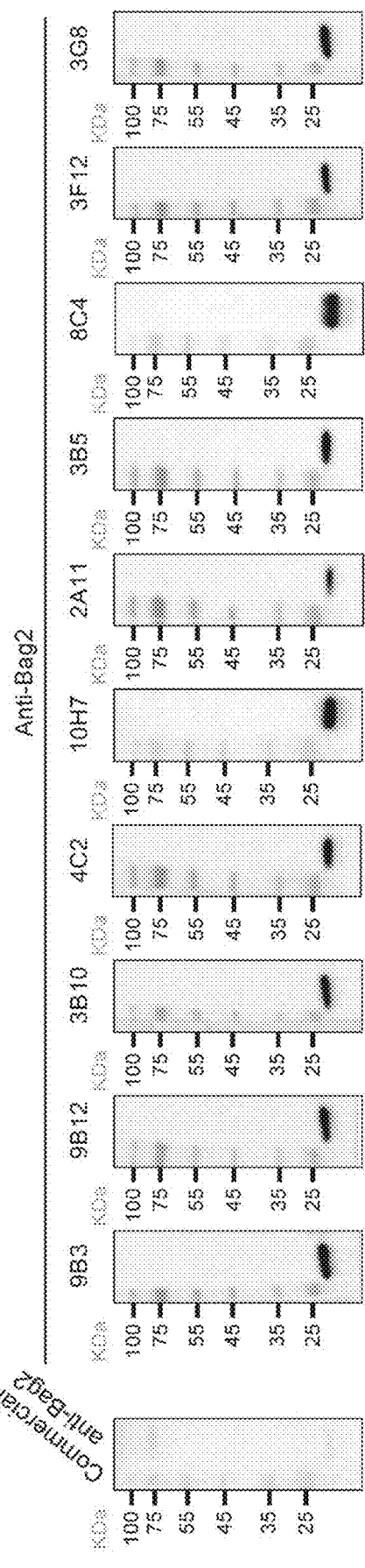
FIG. 1 shows the results of Western blotting of anti-BAG2 antibodies produced from 10 mouse hybridoma cells.

The following examples are offered by way of illustration of the present invention, and not by way of limitation.

EXAMPLES

Example 1: Selection, Sequencing and Antigen-Antibody Reaction of Anti-Bag2 Antibody 1. Selection of Monoclonal Antibodies Targeting Bag2 and Analysis of Amino Acid Sequences Thereof The inventors selected antibodies targeting Bag2, analyzed their amino acid sequences, and determined the complementarity determining region (CDR) of each of the antibodies.

In detail, a gene consisting of the nucleotide sequence of SEQ ID NO: 70 encoding the human BAG2 protein consisting of the amino acid sequence of SEQ ID NO: 69 was cloned into a pCAGGS plasmid and linearized, and then the linearized construct was inoculated into the muscles of five 6-week-old female BALB/c mice by the appliance of electroshock. The construct was inoculated intramuscularly three times at three-week intervals, and consisted of 100 ug of DNA in 100 ul of PBS. At this time, the plasmid of the control group was also subjected to the same manner. To produce therapeutic and diagnostic antibodies, a more efficient DNA vaccine-based immunization strategy than protein-based antigen injection was performed. Blood was collected from the fundus vena cava or the caudal vein of the mouse, and examined by enzyme immunoassay showing the serum antibody titer, and spleens were extracted 3 days after the last immunization from the mouse showing sufficient antibody titer. B lymphocytes were isolated from the spleen, followed by fusion with the myeloma cells cultured with the isolated B lymphocytes, that is, the SP2/0-Ag14 cell line of ATCC, thereby obtaining fused cells. After fused cells were cultured in HAT medium containing hypoxanthin, aminopterine, and thymidine, hybridoma cells fused only with myeloma and B lymphocytes were obtained by selecting approximately 130 clones. Of the hybridoma cells obtained through the selection process by immunoblotting, 10 hybridoma cells producing antibodies specifically binding to human BAG2 protein were obtained.

Total RNA of anti-BAG2 antibodies was produced from the $5\times10^6$ hybridoma cells, and 5'-RACE-cDNA was produced from 100 ng total RNA by using SMART RACE cDNA Amplification kit (Clontech) according to the instructions of the manufacturer. A heavy chain variable region (VH) and a light chain variable region (VL) coding regions were amplified by PCR, and the amplified genes were inserted into the pGEM-T vector (Promega, USA), cloned, and nucleotide sequences thereof were analyzed by using an automated genetic analyzer (ABI Prism 310, Applied Biosystem Co.). The nucleotide sequences of the analyzed genes were identified by comparison with the previously reported nucleotide sequence, and the identified nucleotide sequences were artificially translated for use in determining sequences of complementarity determining regions VH-CDR1, -CDR2, and -CDR3 and VL-CDR1, -CDR2, and -CDR3. The determining the sequences of complementarity determining regions was performed using Kabat's database (http://www.bioinf.org.uk/abs/).

As a result, 10 anti-BAG2 antibodies specifically binding to BAG2 were obtained from the hybridoma cells. 10 anti-BAG2 antibodies were 2A11, 4C2, 8C4, 3B5, 9B3, 9B12, 3B10, 10H7, 3 GB, and 3F12 antibodies. In addition, the amino acid sequences of a heavy chain variable region, a light chain variable region and complementarity determining regions thereof as shown in Tables 1 to 3 and the nucleotide sequences of the genes encoding the antibodies were determined.

2A11, 4C2, and 8C4 antibodies include a heavy chain variable region consisting of an amino acid sequence of SEQ ID NO: 21 and a light chain variable region consisting of an amino acid sequence of SEQ ID NO: 27. In the 2A11 antibody, the 56th and 57th Xaa of SEQ ID NO: 21 are each Gly and the 53rd Xaa of SEQ ID NO: 27 is lie. In the 4C2 antibody, 56th Xaa and 57th Xaa of SEQ ID NO: 21 are Gly and Ala, respectively, and 53rd Xaa of SEQ ID NO: 27 is Phe. In the 8C4 antibody, 56th Xaa and 57th Xaa of SEQ ID NO: 21 are Ala and Gly, respectively, and 53rd Xaa of SEQ ID NO: 27 is Phe.

VH-CDR1, -CDR2 and -CDR3 of 2A11, 4C2, and 8C4 antibodies consist of amino acid sequences of SEQ ID NOS: 33, 39 and 45, respectively, and VL-CDR1, -CDR2 and -CDR3 consist of amino acid sequences of SEQ ID NOS: 51, 57, and 63, respectively. In 2A11 antibody, 56th and 57th Xaa of SEQ ID NO: 21 each are Gly. Regarding 4C2 antibody, in SEQ ID NO: 21, 56th Xaa is Gly and 57th Xaa is Ala. Regarding 8C4 antibody, in SEQ ID NO: 21, 56th Xaa is Ala and 57th Xaa is Gly.

9B3, 9B12 and 3B10 antibodies include a heavy chain variable region consisting of an amino acid sequence of SEQ ID NO: 23 and a light chain variable region consisting of an amino acid sequence of SEQ ID NO: 29. Regarding 9B3 antibody, in SEQ ID NO: 23, 1st Xaa is Glu, 7th Xaa is Ser, 12th Xaa is Val, 27th Xaa is Tyr, 58th Xaa is Ser, 61st Xaa is Asn, 74th Xaa is Lys, 83rd Xaa is Phe, 92nd Xaa is Ala, and 108th Xaa is Tyr. Regarding 9B3 antibody, in SEQ ID NO: 29, 29th Xaa is Ile, 51th Xaa is Ala, 79th Xaa is Glu, and 106th Xaa is Ile. Regarding 9B12 antibody, in SEQ ID NO:23 1st Xaa is Gln, 7th Xaa is Ser, 12th Xaa is Val, 27th Xaa is Tyr, 58th Xaa is Ser, 61st Xaa is Asn, 74th Xaa is Arg, 83rd Xaa is Phe, 92nd Xaa is Gly, and 108th Xaa is His. Regarding 9B12 antibody, in SEQ ID NO: 29, 29th Xaa is Met, 51th Xaa is Ala, 79th Xaa is Glu, and 106th Xaa is Met. Regarding 3B10 antibody, in SEQ ID NO: 23, 1st Xaa is Gln, 7th Xaa is Pro, 12th Xaa is Ala, 27th Xaa is His, 58th Xaa is Thr, 61st Xaa is Ser, 74th Xaa is Arg, 83rd Xaa is Leu, 92th Xaa is Gly, and 108th Xaa is His. Regarding 3B10 antibody, in SEQ ID NO: 29, 29th Xaa is Met, 51th Xaa is Ser, 79th Xaa is Asp, and 106th Xaa is Ile.

Regarding 9B3, 9B12, and 3B10 antibodies, VH-CDR1, -CDR2, and -CDR3 consist of the amino acid sequences of SEQ ID NOS: 35, 41, and 47, respectively, and VL-CDR1, -CDR2, and -CDR3 consist of the amino acid sequences of SEQ ID NOS: 53, 59, and 65, respectively. Regarding 9B3 antibody, 2nd Xaa of SEQ ID NO: 35 is Tyr, 8th Xaa of SEQ ID NO: 41 is Ser, 12th Xaa of SEQ ID NO: 47 is Tyr, 3rd Xaa of SEQ ID NO: 53 is Ile, and 2nd Xaa of SEQ ID NO: 59 is Ala. Regarding 9B12 antibody, 2nd Xaa of SEQ ID

TABLE 1

| Antibody Name | Nucleotide sequence of the VH gene | Nucleotide Sequence of the VL gene |
| --- | --- | --- |
| 2A11 | SEQ ID NO: 1 | SEQ ID NO: 11 |
| 4C2 | SEQ ID NO: 2 | SEQ ID NO: 12 |
| 8C4 | SEQ ID NO: 3 | SEQ ID NO: 13 |
| 3B5 | SEQ ID NO: 4 | SEQ ID NO: 14 |
| 9B3 | SEQ ID NO: 5 | SEQ ID NO: 15 |
| 9B12 | SEQ ID NO: 6 | SEQ ID NO: 16 |
| 3B10 | SEQ ID NO: 7 | SEQ ID NO: 17 |
| 10H7 | SEQ ID NO: 8 | SEQ ID NO: 18 |
| 3G8 | SEQ ID NO: 9 | SEQ ID NO: 19 |
| 3F12 | SEQ ID NO: 10 | SEQ ID NO: 20 |

TABLE 2

| Antibody Name | Amino acid sequence of the VH region | Amino acid sequence of the VL region |
| --- | --- | --- |
| 2A11 | SEQ ID NO: 21 | SEQ ID NO: 27 |
| 4C2 | SEQ ID NO: 21 | SEQ ID NO: 27 |
| 8C4 | SEQ ID NO: 21 | SEQ ID NO: 27 |
| 3B5 | SEQ ID NO: 22 | SEQ ID NO: 28 |
| 9B3 | SEQ ID NO: 23 | SEQ ID NO: 29 |
| 9B12 | SEQ ID NO: 23 | SEQ ID NO: 29 |
| 3B10 | SEQ ID NO: 23 | SEQ ID NO: 29 |
| 10H7 | SEQ ID NO: 24 | SEQ ID NO: 30 |
| 3G8 | SEQ ID NO: 25 | SEQ ID NO: 31 |
| 3F12 | SEQ ID NO: 26 | SEQ ID NO: 32 |

TABLE 3

| Antibody Name | Amino acid sequence of VH-CDR1 | Amino acid sequence ofVH-CDR2 | Amino acid sequence of VH-CDR3 | Amino acid sequence of VL-CDR1 | Amino acid sequence of VL-CDR2 | Amino acid sequence of VL-CDR3 |
| --- | --- | --- | --- | --- | --- | --- |
| 2A11 | SEQ ID NO: 33 | SEQ ID NO: 39 | SEQ ID NO: 45 | SEQ ID NO: 51 | SEQ ID NO: 57 | SEQ ID NO: 63 |
| 4C2 | SEQ ID NO: 33 | SEQ ID NO: 39 | SEQ ID NO: 45 | SEQ ID NO: 51 | SEQ ID NO: 57 | SEQ ID NO: 63 |
| 8C4 | SEQ ID NO: 33 | SEQ ID NO: 39 | SEQ ID NO: 45 | SEQ ID NO: 51 | SEQ ID NO: 57 | SEQ ID NO: 63 |
| 3B5 | SEQ ID NO: 34 | SEQ ID NO: 40 | SEQ ID NO: 46 | SEQ ID NO: 52 | SEQ ID NO: 58 | SEQ ID NO: 64 |
| 9B3 | SEQ ID NO: 35 | SEQ ID NO: 41 | SEQ ID NO: 47 | SEQ ID NO: 53 | SEQ ID NO: 59 | SEQ ID NO: 65 |
| 9B12 | SEQ ID NO: 35 | SEQ ID NO: 41 | SEQ ID NO: 47 | SEQ ID NO: 53 | SEQ ID NO: 59 | SEQ ID NO: 65 |
| 3B10 | SEQ ID NO: 35 | SEQ ID NO: 41 | SEQ ID NO: 47 | SEQ ID NO: 53 | SEQ ID NO: 59 | SEQ ID NO: 65 |
| 10H7 | SEQ ID NO: 36 | SEQ ID NO: 42 | SEQ ID NO: 48 | SEQ ID NO: 54 | SEQ ID NO: 60 | SEQ ID NO: 66 |
| 3G8 | SEQ ID NO: 37 | SEQ ID NO: 43 | SEQ ID NO: 49 | SEQ ID NO: 55 | SEQ ID NO: 61 | SEQ ID NO: 67 |
| 3F12 | SEQ ID NO: 38 | SEQ ID NO: 44 | SEQ ID NO: 50 | SEQ ID NO: 56 | SEQ ID NO: 62 | SEQ ID NO: 68 |

NO: 35 is Tyr, 8th Xaa of SEQ ID NO: 41 is Ser, 12th Xaa of SEQ ID NO: 47 is His, 3rd Xaa of SEQ ID NO: 53 is Met, and 2nd Xaa of SEQ ID NO: 59 is Ala. Regarding 3B10 antibody, 2nd Xaa of SEQ ID NO: 35 is His, 8th Xaa of SEQ ID NO: 41 is Thr, 12th Xaa of SEQ ID NO: 47 is His, 3rd Xaa of SEQ ID NO: 53 is Met, and 2nd Xaa of SEQ ID NO: 59 is Ser.

2. Identification of Antigen-Antibody Responses of Anti-BAG2 Antibodies in Breast Cancer Cells FIG. 1 shows the results of immunoblotting of anti-BAG2 antibodies produced from 10 mouse hybridoma cells. Specifically, MDA-MB-231 cells, which are human breast cancer cells, were cultured in DMEM (Welgene) medium containing 10% FBS, 100 U/ml penicillin and 100 μg/ml streptomycin at a temperature of 37° C. The cells were harvested from wells and washed with PBS, and dissolved in a lysis buffer solution containing 1% Brij 97, 5 mM EDTA, 0.02M HEPES pH 7.3, 0.15M NaCl, 1 mM PMSF, 0.5 mM NaF, 10 µg/rni aprotinin, and 0.2 mM sodium orthovanadate. After 15 minutes of incubation on ice, the nuclei were removed from the cells by centrifugation and the supernatants were collected. 2× sample buffer consisting of 20% glycerol, 4.6% SOS, 0.125M tris, pH 6.8, 0.1% bromophenol blue was added to an appropriate amount of the supernatants. 10 ug protein samples were subjected to SOS-PAGE analysis on a 12% gel under standard conditions by using a mini-Protean II system (Bio-Rad Hercules, Calif.). For immune blotting, the protein was transferred to Millipore, a PVDF membrane. A blocking solution consisting of 0.1% Tween 20 and 5% bovine serum albumin (BSA) in TBS was allowed to react for 1 hour. Subsequently, the primary antibody was a 1/2000 dilution of anti-BAG2 antibody extracted from hybridoma cell culture, and the goat anti-mouse HRP conjugate (Dako) used as the secondary antibody was diluted to 1/5000. Film-photosensing was carried out in the dark using EGL reagent (Amersham Pharmacia Biotech) as a substrate. The photosensitized bands were compared to standard molecular markers to identify the bands corresponding to the size of BAG2.

As a result, as shown in FIG. 1, compared with the ab58682 (Abcam), a commercial polyclonal anti-BAG2 antibody used as a positive control, the antibodies 2A11, 3B5, 3B10, 3F12, 3 GB, 4C2, 8C4, 9B3, 9B12 and 10H7 showed antigen-antibody reactions, targeting BAG2.

Next, for domain mapping of the BAG2 antigen to which the ten antibodies identified in Section 1 above, cells, to which the GST-Empty vector (pcDNA3.1+/GST vector, NovoPro Bioscience Inc. China) having a molecular weight of about 26 kDa was introduced, was used as a negative control. GST-Bag Full vector, GST-Bag F1 vector, GST-Bag F2 vector, GST-Bag F3 vector, and GST-Bag F4 vector, each including polynucleotides encoding human BAG2 protein and polynucleotides encoding fragments of the BAG2 protein, were introduced into cells, and the cells with the vectors introduced thereinto were cultured to express the genes, and then, cell lysates were obtained. For cell lysates, immunoblotting was performed using each of the 10 antibodies. The polynucleotide encoding the human BAG2 protein has the nucleotide sequence of SEQ ID NO: 70. The GST-Bag F1, -Bag F2, -Bag F3, and -Bag F4 vectors consist of the nucleotide sequences of SEQ ID NOS: 71 to 74, respectively.

Figure 2A:
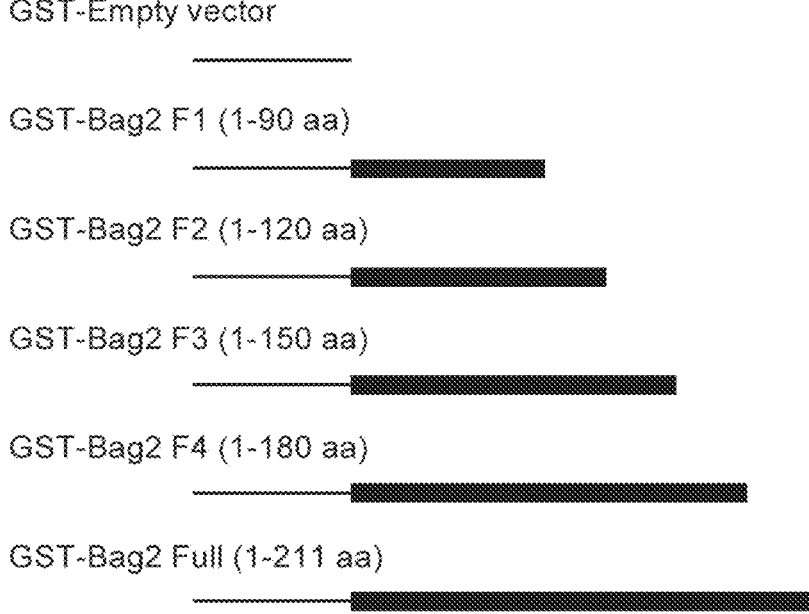
FIGS. 2A and 2B show the results of Western blotting for the full-length BAG2 polypeptide of anti-BAG2 antibody or a fragment thereof.
Figure 2B:
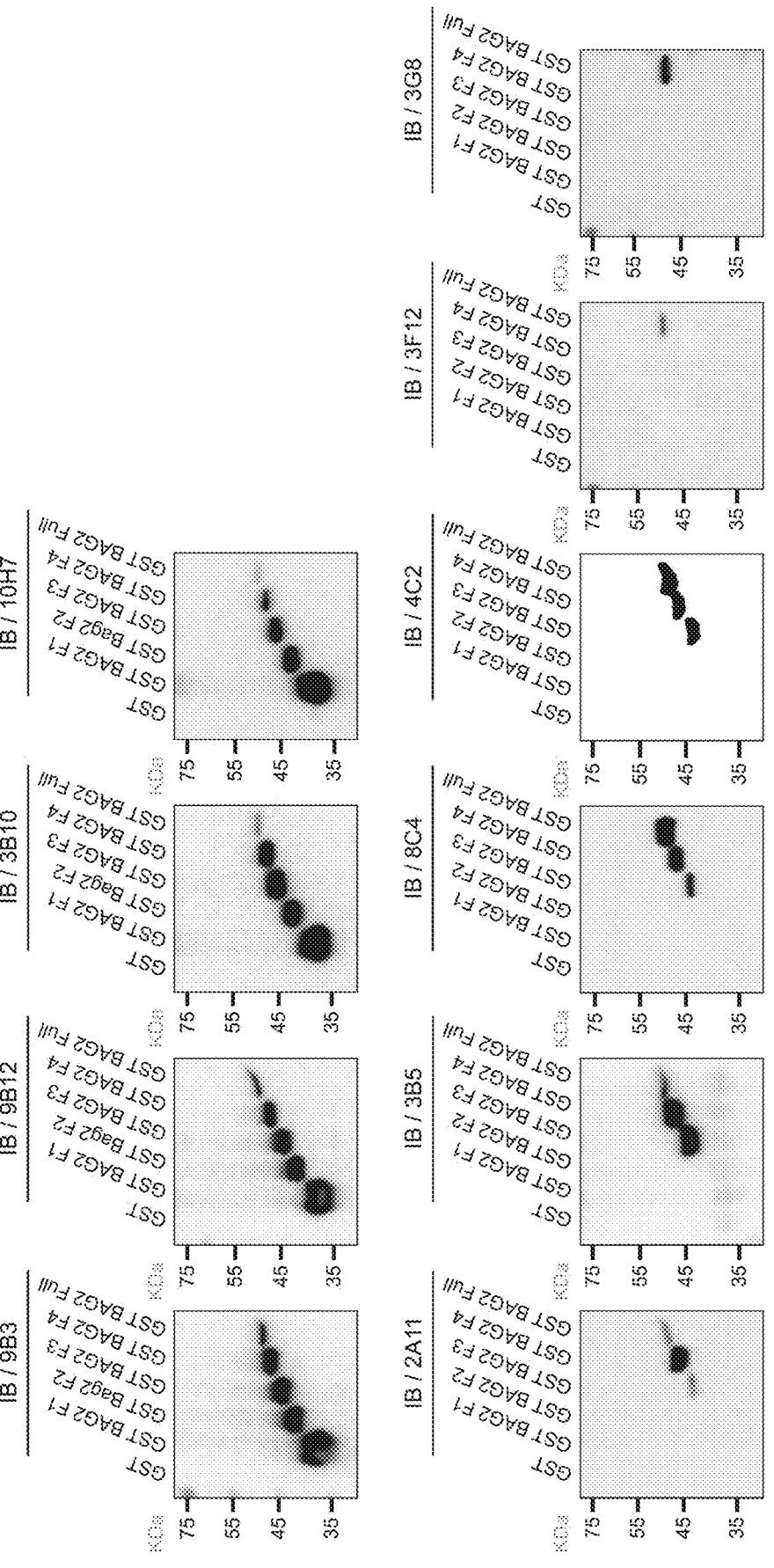

FIGS. 2A and 2B show the results of immunoblotting for the full-length BAG2 polypeptide of anti-BAG2 antibody or a fragment thereof. In FIG. 2, A shows diagrams of the vectors and BAG2 proteins and fragments thereof, and B shows the results of immunoblotting. In detail, the immunoblotting was performed as follows: each of the vectors was introduced into HEK293T cells by lipofectamine transfection (Thermo Fisher Scientific, Inc., Waltham, MA, USA) method, and the obtained transformed cells were cultured at a temperature of 37° C. in DMEM (Welgene) medium containing 10% FBS, 100 U/ml penicillin and 100 µg/ml streptomycin for 30 hours, and then cells were isolated. The isolated cells were disrupted using the same method as described in connection with FIG. 1 and subjected to SOS-PAGE analysis on a 12% gel. For immunoblotting, after reacting for 1 hour with the same blocking solution as described in connection with FIG. 1, each of the 10 purified anti-BAG2 antibodies having a concentration of 2 mg/ml was used as a primary antibody at a dilution of 1/10000 dilution and bound to the cells. The goat anti-mouse HRP conjugate used as the secondary antibody was used at a 1/5000 dilution concentration, and Film-photosensing was carried out in the dark using EGL reagent (Amersham Pharmacia Biotech) as a substrate. Standard molecular marker sizes were expressed to confirm the size of BAG2.

As a result, as shown in FIG. 2, each anti-BAG2 antibody was differentially bound to the full-length BAG2 polypeptide or fragments thereof. In particular, for each of the 10 anti-BAG2 antibodies, signals were commonly detected at the position of about 50 kDa in GST-Bag Full vector-introduced cell lysates. This result shows that all of these antibodies can bind to full-length BAG2 polypeptides. Finally, the domain region of BAG2 to which each anti-BAG2 antibody reacts was identified.

Figure 3:
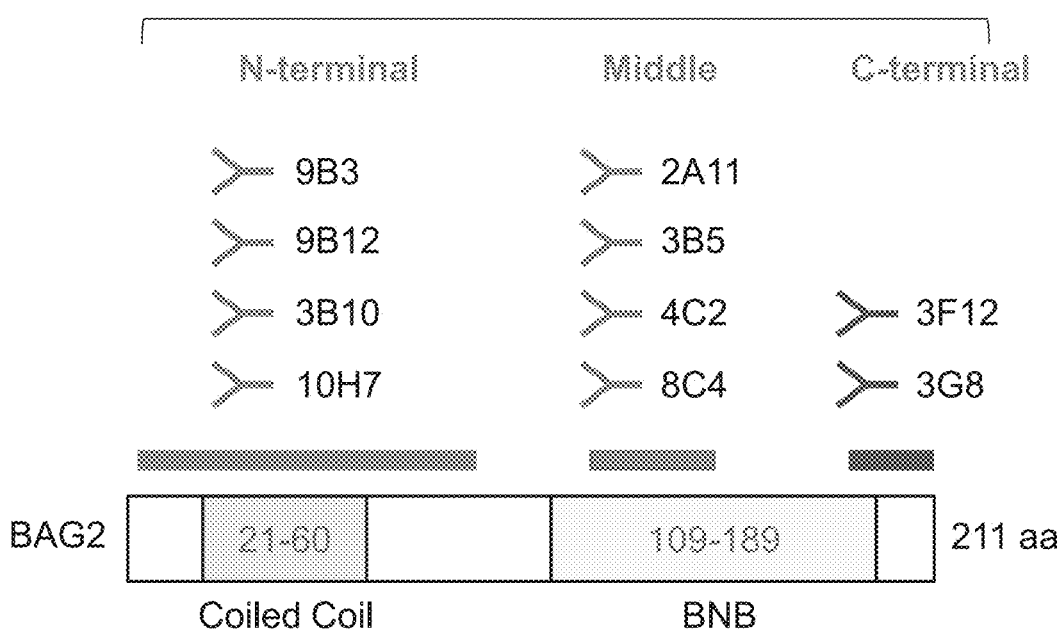
FIG. 3 shows a BAG2 domain which reacts with respective anti-BAG2 antibodies.

FIG. 3 shows a BAG2 domain which reacts with respective anti-BAG2 antibodies. As shown in FIG. 3, 9B3, 9B12, 3B10, and 10H7 antibodies were bound to the N-terminus of BAG2 protein, 2A11, 3B5, 4C2, and 8C4 antibodies were bound to a middle region of BAG2 protein, and 3F12 and 3 GB antibodies were bound to the C-terminus of BAG2 protein. The N-terminus commonly includes a coiled coil region of 21-60 amino acids, and the middle region is bound to a portion of the BNB region of 109-189 amino acids. Therefore, by using a set of antibodies that bind to different sites, the BAG2 protein or its fragments present in the sample may be detected with high sensitivity and specificity.

Figure 4:
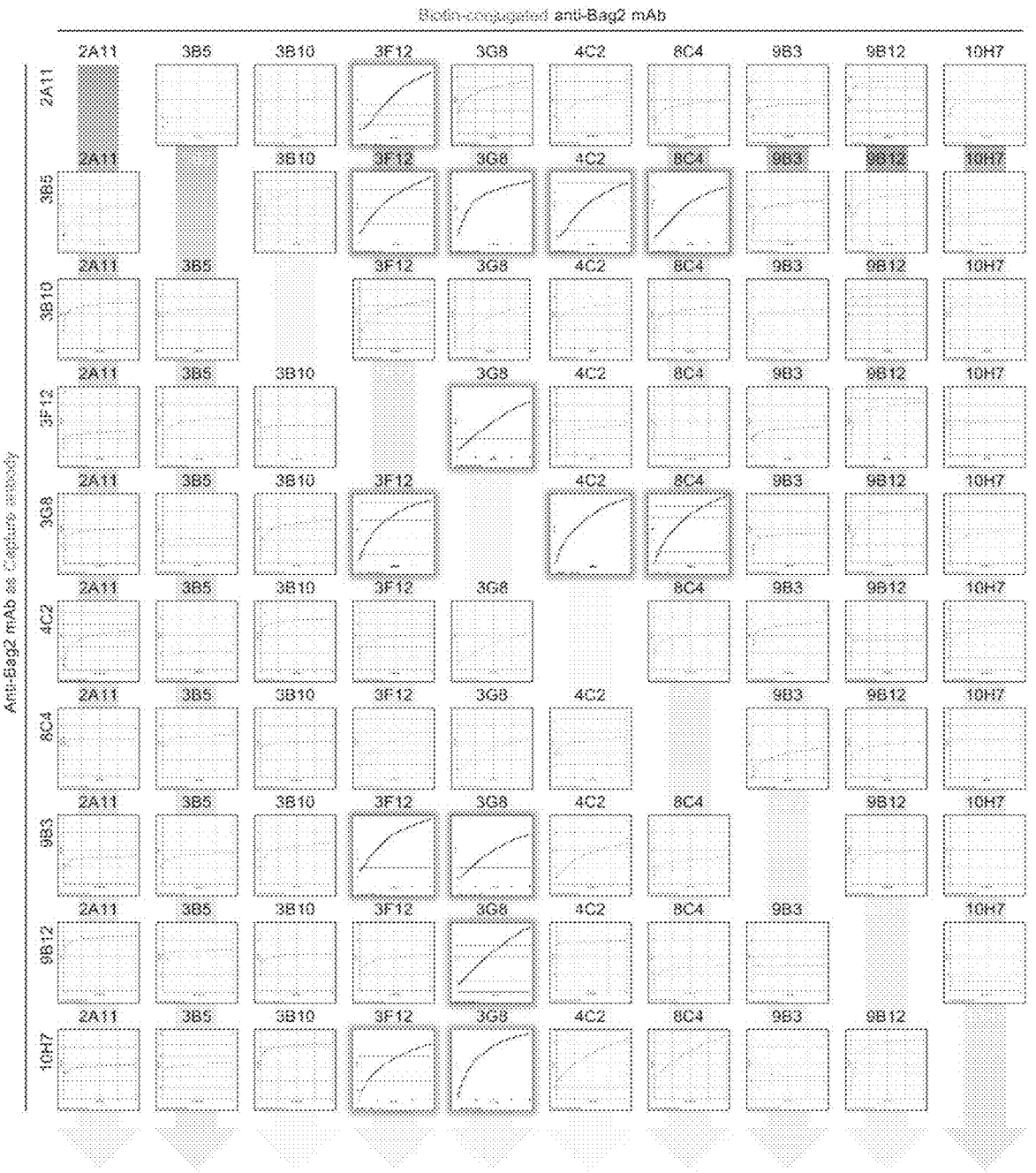
FIG. 4 shows standard curves for BAG2 protein in possible 90 combinations of anti-BAG2 antibodies.

Example 2: Screening of Combinations of Anti-BAG2 Antibodies and Confirmation of Cancer Diagnostic Efficacy 1. Screening of Combinations of Anti-BAG2 Antibodies Useful for Cancer Diagnosis FIG. 4 shows standard curves for BAG2 protein in possible 90 combinations of anti-BAG2 antibodies. As a result, as shown in FIG. 4, from among possible combinations of anti-BAG2 antibodies, 14 antibody combinations showing a standard curve of high slope, 2A11-3F12, 10H7-3G8, 9B12-3G8, 10H7-3F12, 9B8-3G8, 3G8-3F12, 3B5-3F12, 3G8-4C2, 3F12-3G8, 3B5-3G8, 3B5-4C2, 3G8-8C4, and 9B3-3F12, were selected.

Figure 5:
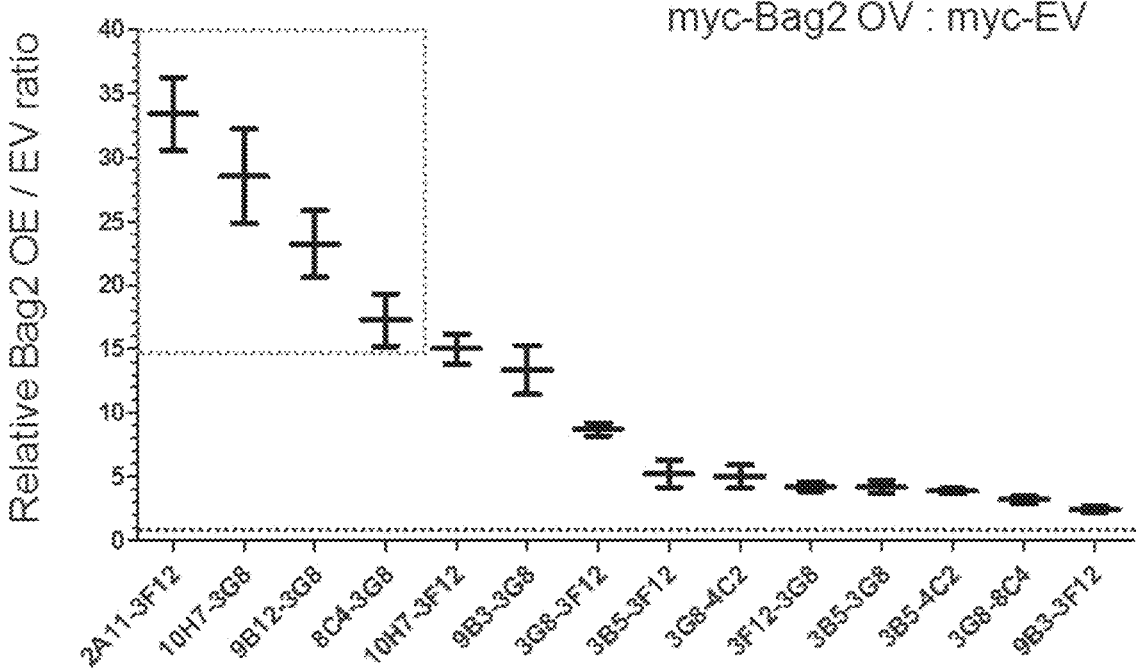
FIG. 5 shows a diagram showing the specific binding force of the selected 14 antibody combinations with respect to the BAG2 protein.

FIG. 5 shows a diagram showing the specific binding force of the selected 14 antibody combinations with respect to the BAG2 protein. In detail, Myc-tag BAG2 expression vector or Myc-tag empty vector was each transduced into the human breast cancer cell line MDA-MB-231 by using Lipofectamine 2000 (Invitrogen) according to the instructions of the manufacturer. Using 14 antibody combinations, relative amounts of BAG2 protein secreted from 30 ug of lysate of control cells into which Myc-tag empty vector was introduced and cells overexpressing BAG2 protein into which Myc-tag BAG2 expression vector were introduced, were determined. Control cells were labeled with EV and BAG2 overexpressing cells were labeled with OE. That is, by confirming the relative amount of the secreted BAG2 protein of BAG2 overexpressing cells and control cells, it is possible to determine the specific binding capacity of the antibody combination with respect to the BAG2 protein.

As a result, as shown in FIG. 5, four antibody combinations, 2A11-3F12, 9B12-3G8, 8C4-3G8, and 10H7-3F12, having high specific binding ability to BAG2 protein were selected.

2. Identification of Efficacy of Selected Anti-BAG2 Antibody Combinations in Diagnosis of Various Cancer In order to confirm the cancer diagnostic efficacy of the antibody combinations selected in Section 1, the antigen-antibody reaction of the antibody combinations with BAG2 was confirmed. In detail, human BAG2 protein having 6 histidine attachments to N-terminus produced and purified from human 293T cells was obtained as an antigen.

Sandwich enzyme-linked immunosorbent assay (Sandwich ELISA) was performed using each of the 2A11-3F12, and 9B12-3G8 antibody combinations.

In detail, Sandwich ELISA was performed through the following process. Each of antibodies 3F12 and 3G8 was reacted in an amount of 1 mg with 27 ul of 10 mM NHS-biotin (Succinimidyl Biotin, Thermo scientific, Cat #21435) to prepare a biotin-bound detecting antibody. Each of antibodies 2A11, 9B12, 8C4, and 10H7 as a capturing antibody was diluted to a concentration of 3 ug/ml by using an ELISA plate-coating buffer (R&D system, DY006), and spread in amount of 100 ul in each well of a 96 well plate, and then, coated at the temperature of 4° C. overnight. Antibody-coated plates were blocked with 1% bovine serum albumin (BSA) buffer (R&D system, DY995) for 1 hour at room temperature. As a BAG2 standard material, human His-tagging BAG2 recombinant proteins (Ybiologics, Korea) produced in human-derived cell line HEK293T and purified were prepared at the concentration of 100 ng/ml using the 1% BSA buffer, and then, diluted 4 fold to prepare 0.02, 0.097, 0.31, 1.56, 6.25, and 25 ng/ml of standard solutions. For blood samples, 8 ml or more of blood was collected from each of 14 healthy people, 20 patients diagnosed with luminal breast cancer, and 38 patients diagnosed with TNBC type breast cancer and then mixed by gently shaking and allowed to stand at room temperature for 20-30 minutes. Then, the blood was centrifuged at 2,500 rpm for 10 minutes. Serum stored below 4° C. was diluted 1/2 fold using the 1% BSA buffer. Into each well of the plate from which the blocking solution was removed, 0, 0.02, 0.097, 0.39, 1.56, 6.25, 25, and 100 ng/ml of the BAG2 standard solutions and 100 ul of the patient sample diluted 1/2 fold were dispensed and reacted at room temperature for 1 hour, and then, washed with a washing buffer (R&D system, WA126). 100 ul of streptavidin-HRP (Pierce, 21130) diluted 1:50000 by using 1% BSA buffer was dispensed into each well and reacted for 30 minutes at room temperature, followed by washing with a washing buffer. 100 ul of 3,3',5,5'-tetramethylbenzidine (TMB, R &D system, DY999) was dispensed into each well, reacted for 15 minutes at room temperature in female cow, and then, a stop solution was added thereto to stop the reaction. The concentration of BAG2 protein in the patient sample was calculated from the standard curve of the antibody obtained by measuring the absorbance of the reaction solution at 450 nm.

Figure 6A:
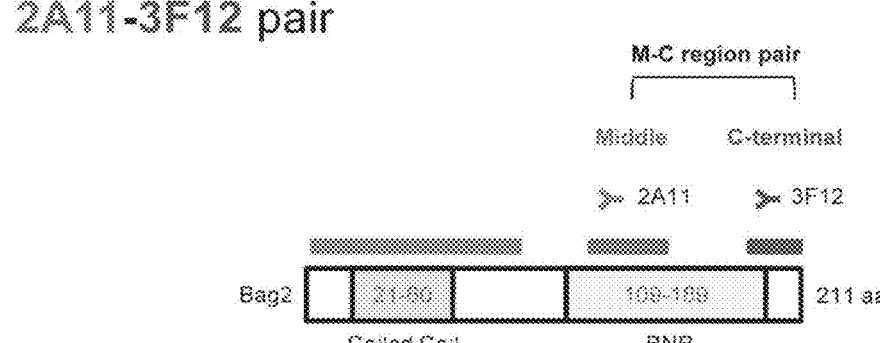
FIGS. 6A and 6B shows differences in BAG2 expression patterns in various cancer cell lines observed using the antibody combination of 2A11-3F12 and the antibody combination of 9B 12-3G8.
Figure 6A:
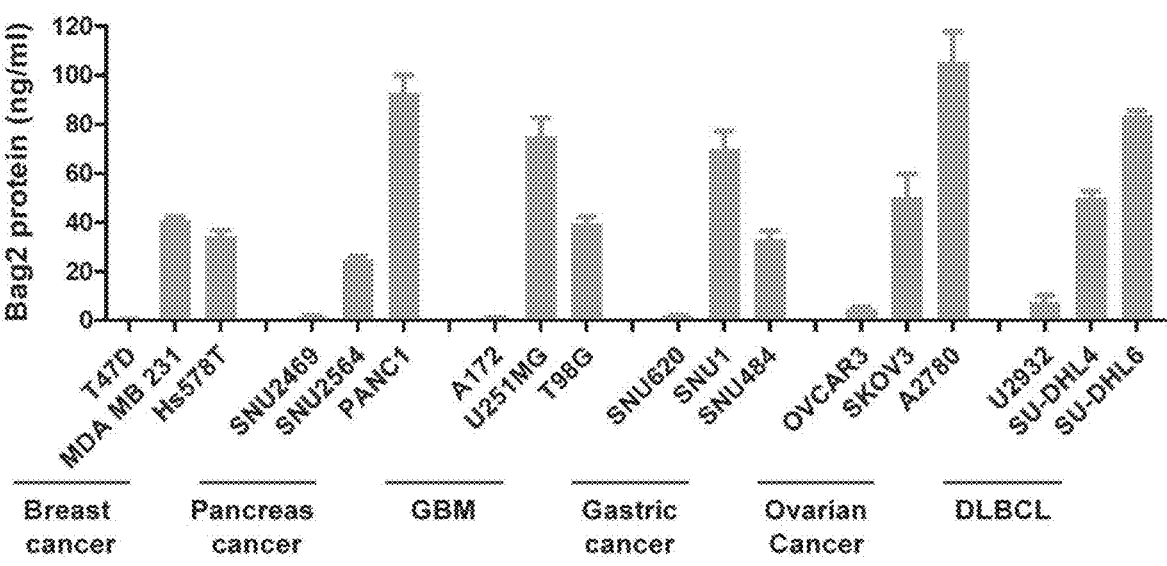
Figure 6B:
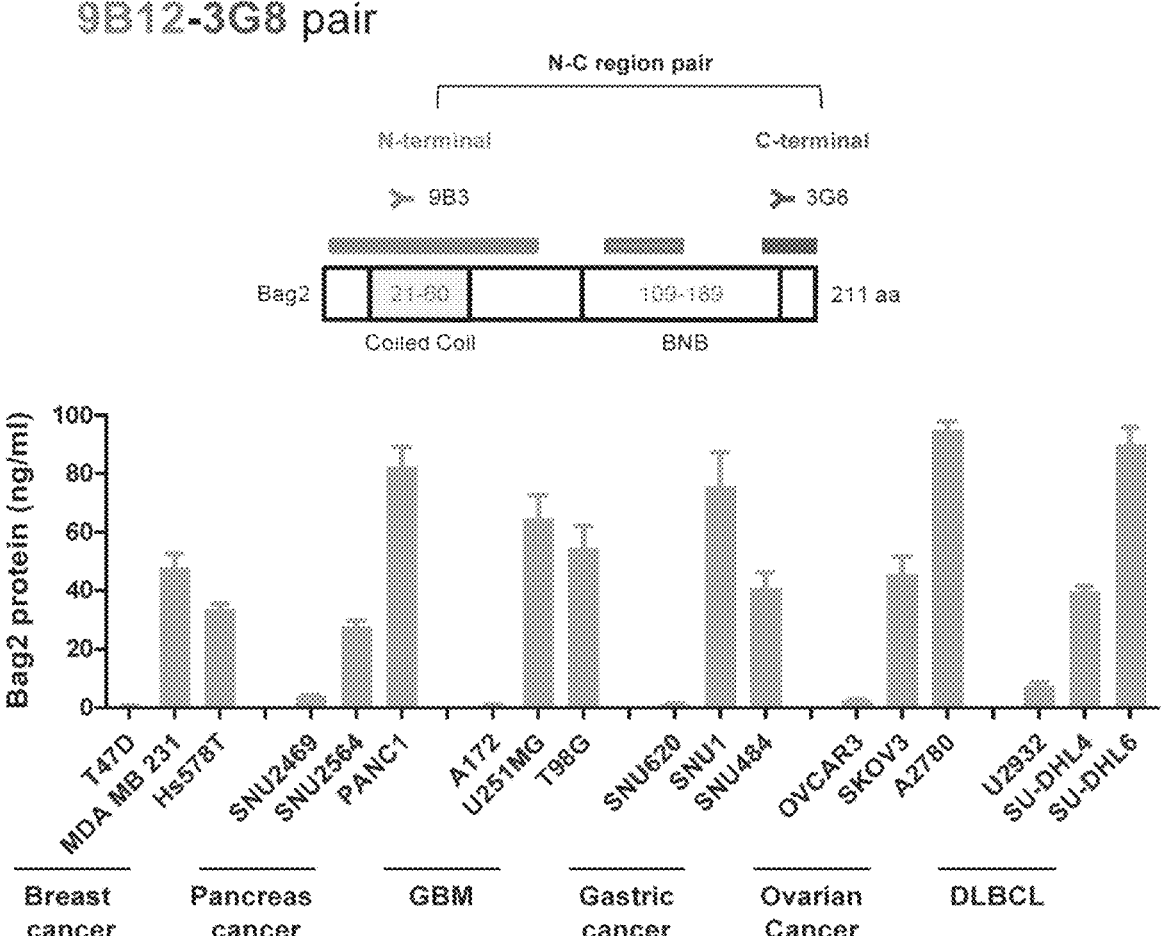

FIG. 6 shows differences in BAG2 expression patterns in cancer cell lines including breast cancer, pancreatic cancer, glioblastoma multiforme, gastric cancer, ovarian cancer, and diffuse giant B cell lymphoma which were observed by using anti-BAG2 antibody combinations. FIG. 6A shows the results of sandwich ELISA of 2A11-3F12 antibody combination, and FIG. 6B shows the results of sandwich ELISA of 9B12-3G8 antibody combination.

As illustrated in FIGS. 6A and 6B, when 2A11-3F12, and 9B12-3G8 antibody combinations were used, BAG protein was expressed at high levels in various cancer cell lines including MDA-MB-231 and Hs578T which are breast cancer cell lines, SNU2564 and PANC1 which are pancreatic cancer cell lines, U251MG and T98G which are glioblastoma multiforme (GBM) cell lines, SNU1 and SNU484 which are gastric cancer cell lines, SKOV3 and A2780 which are ovarian cancer cell lines, and SU-DHL4 and SU-DHL6 which are diffuse giant B cell lymphoma (DLBCL) cell lines. In contrast, the BAG2 protein in T47D, SNU2469, A172, SNU620, OVCAR3, and U2932, which are normal cell lines, was not expressed at all or were expressed little. In other words, it was confirmed that the BAG2 protein was significantly highly expressed in cancer cells including breast cancer, pancreatic cancer, glioblastoma multiforme, gastric cancer, ovarian cancer, and diffuse giant B cell lymphoma by using 2A11-3F12, and 9B12-3G8 antibody combinations, compared with normal cells.

Therefore, when the above antibody combinations are used, cancer can be effectively diagnosed by identifying whether the expression pattern of BAG2 protein is similar to that of BAG2 protein showing in cancer cells, compared to normal cells.

3. Identification of Efficacy of Selected Anti-BAG2 Antibody Combinations in Diagnosis of Breast Cancer By using the same Sandwich ELISA method described in Section 2, the difference in the expression pattern of BAG2 protein in serum between luminal type and TNBC type breast cancer patients and normal subjects was confirmed. In detail, the serum of healthy volunteers (N=14), luminal type breast cancer patients (N=20) and TNBC type breast cancer patients (N=38) was collected, and the expression pattern of BAG2 protein in the obtained serum was confirmed.

Figure 7A:
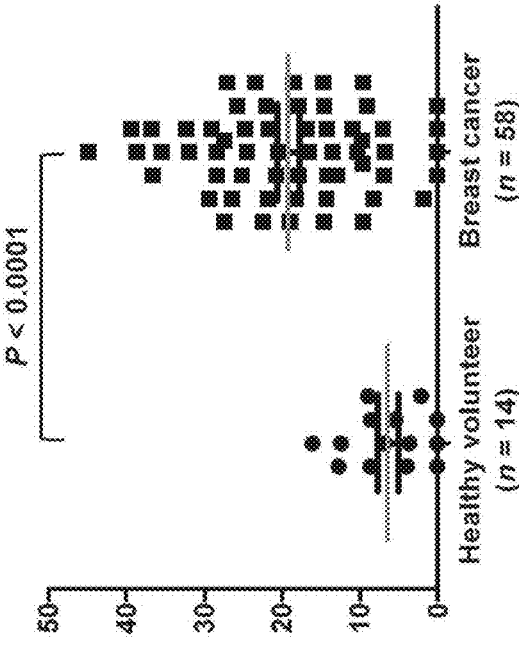
FIGS. 7A and 7B shows significant differences in BAG2 protein expression in the serum of luminal type and TNBC type breast cancer patients observed by using the antibody combination of 2A11-3F12 and the antibody combination of 9B12-3G8.
Figure 7A:
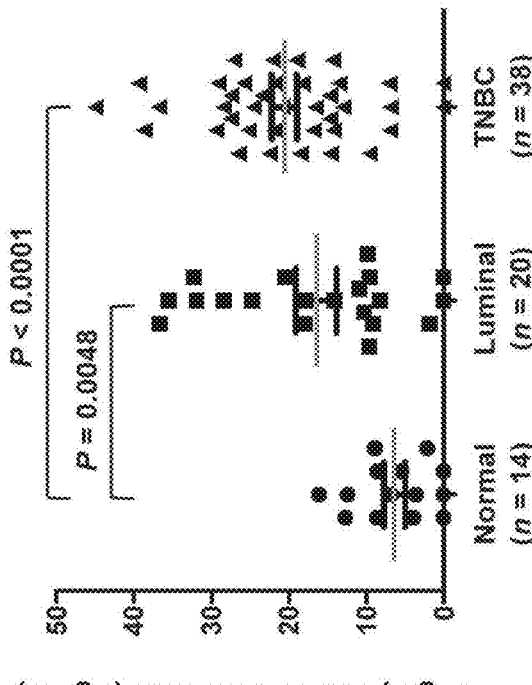
Figure 7B:
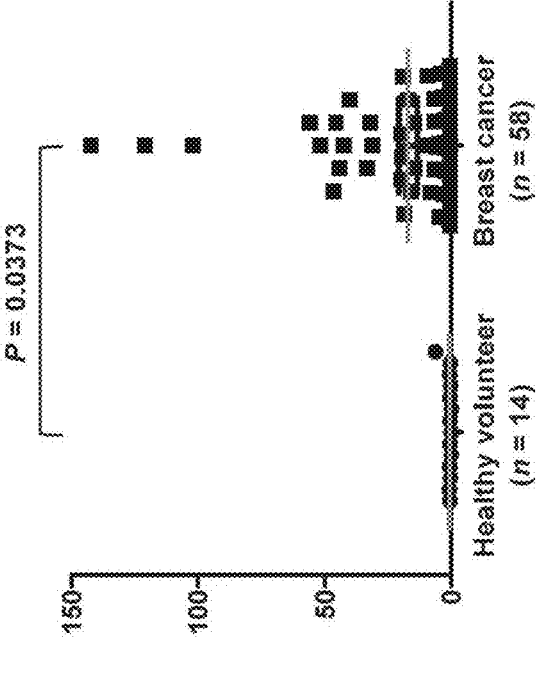
Figure 7B:
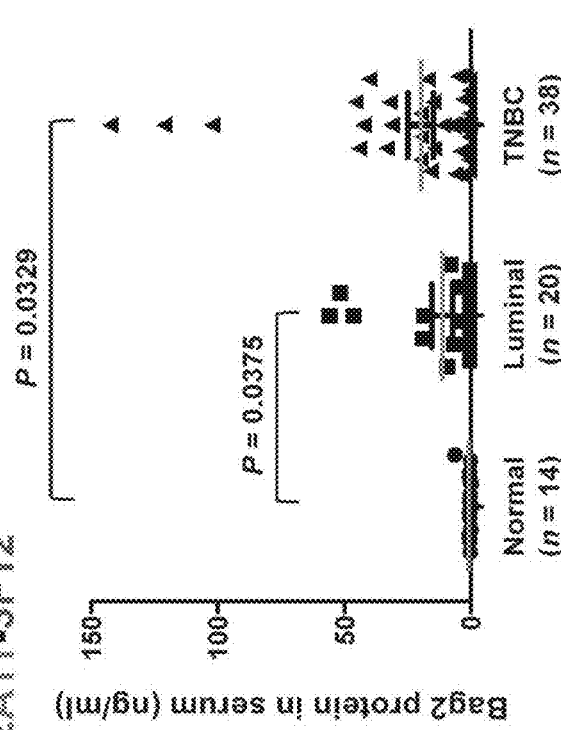
Figure 8A:
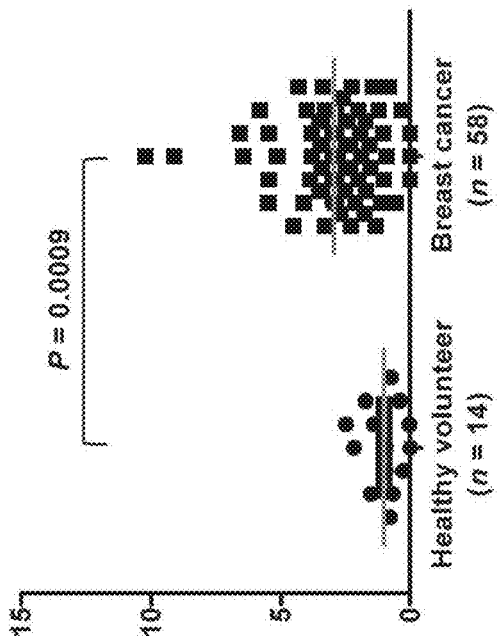
FIGS. 8A and 8B shows significant differences in BAG2 protein expression in the serum of luminal type and TNBC type breast cancer patients observed by using the antibody combination of 8C4-3G8 and the antibody combination of 10H7-3G8.
Figure 8A:
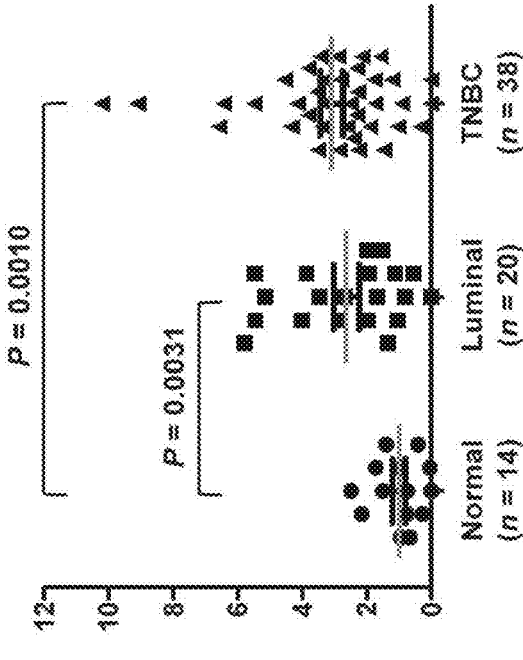
Figure 8B:
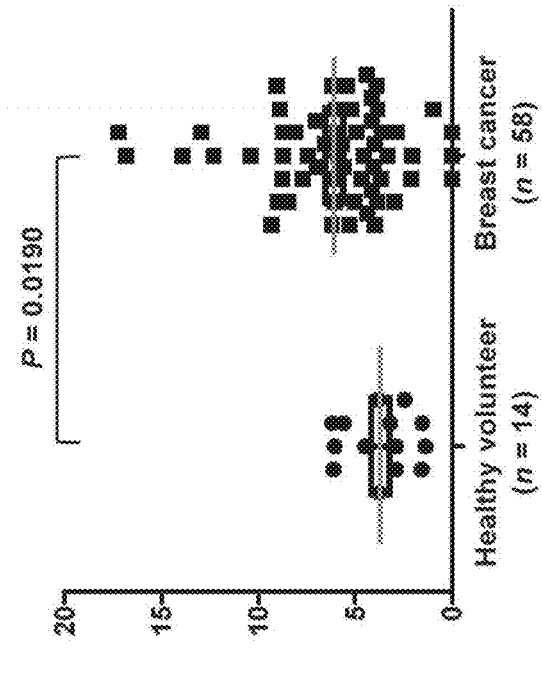
Figure 8B:
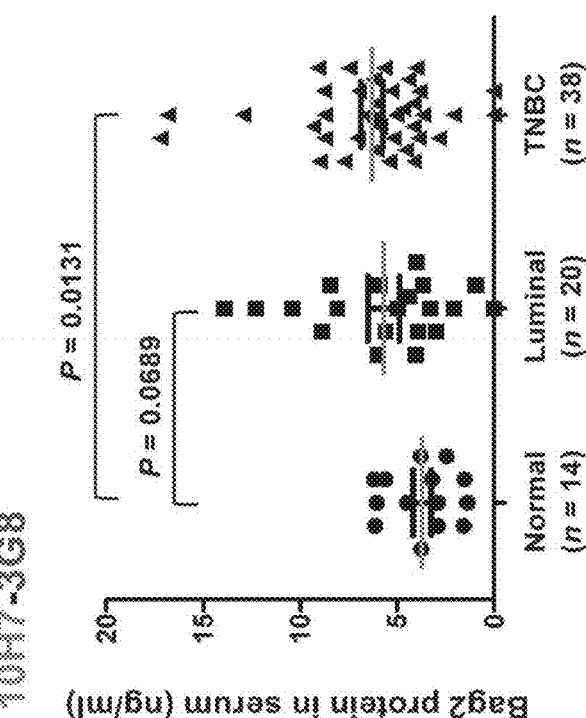

FIGS. 7A and 7B and 8A and 8B show significant differences in BAG2 protein expression in the serum of luminal type and TNBG type breast cancer patients identified by using anti-BAG2 antibody combinations. FIG. 7A shows the case using 9B12-3G8 antibody combination, and FIG. 7B shows the case using 2A11-3F12 antibody combination. FIG. 8A shows the case using 8G4-3G8 antibody combination, and FIG. 8B shows the case using 10H7-3G8 antibody combination.

As shown in FIGS. 7A and 7B and 8A and 8B, when 9B12-3G8, 2A11-3F12, 8G4-3G8, and 10H7-3F12 antibody combinations were used, p-values of the respective antibody combinations were p<0.0001, p=0.0373, p=0.0009, and p=0.0190, indicating that there was a significant difference in BAG2 protein expression patterns in the serum of luminal type and TNBG type breast cancer patients compared to normal subjects. Therefore, by observing significant differences in BAG2 protein expression patterns using the antibody combinations, breast cancer can be effectively diagnosed.

4. Confirmation of the Usefulness of Selected Anti-BAG2 Antibody Combination in Breast Cancer Diagnosis.

In order to confirm the sensitivity and specificity of cancer diagnosis using each of the four antibody combinations, the results of Section 2 are shown by using ROG curves.

Figure 9A:
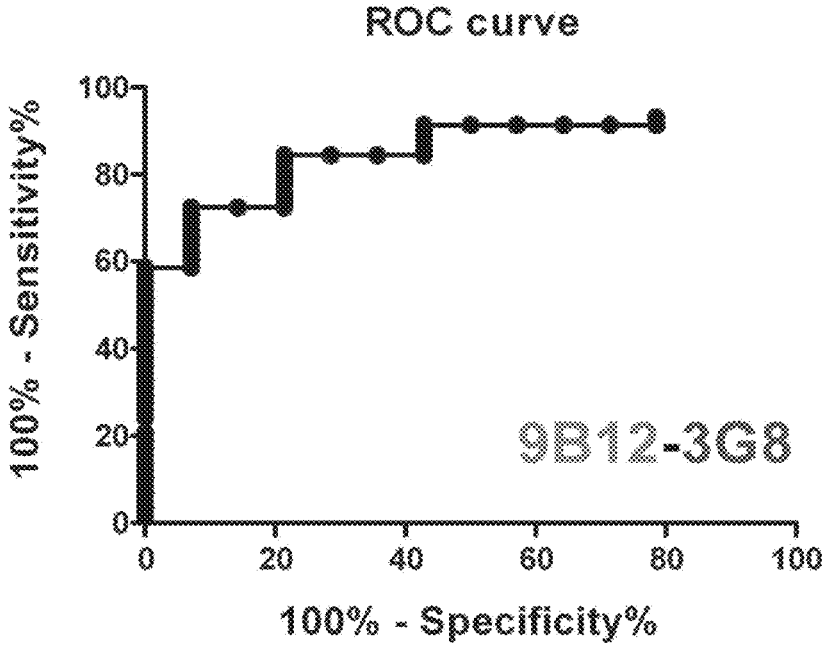
FIGS. 9A, 9B, 9C and 9D show the receiver operating characteristic curve (ROC) values and area under the curve (AUC) values of the four antibody combinations.
Figure 9B:
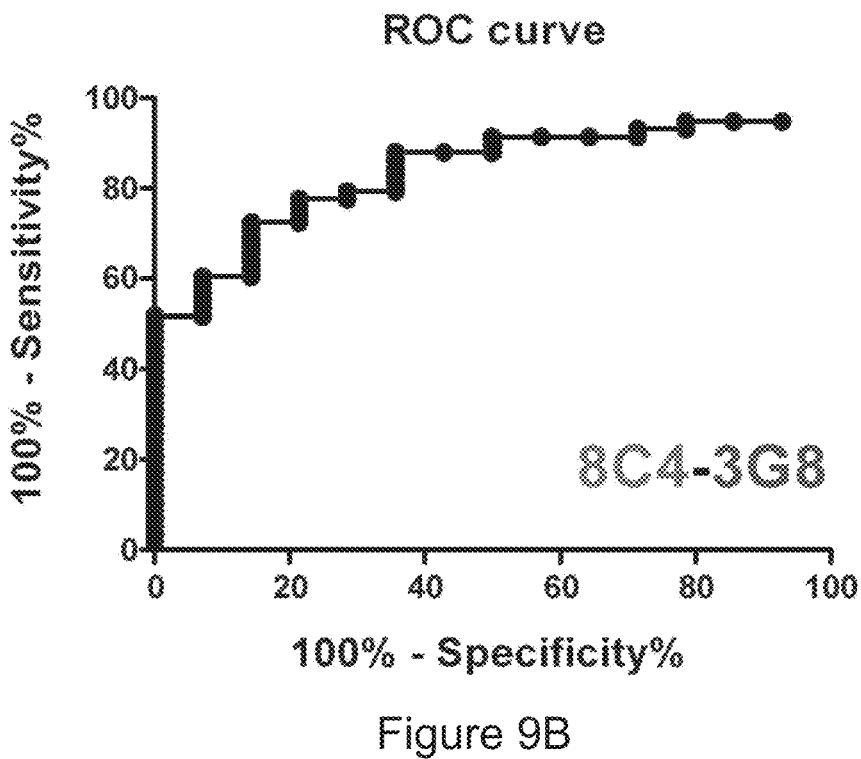
Figure 9C:
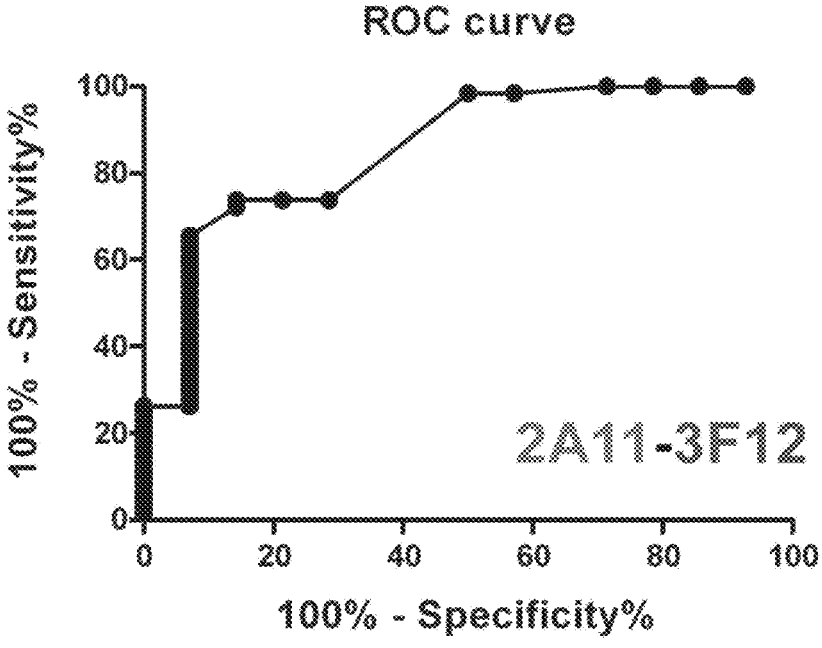
Figure 9D:
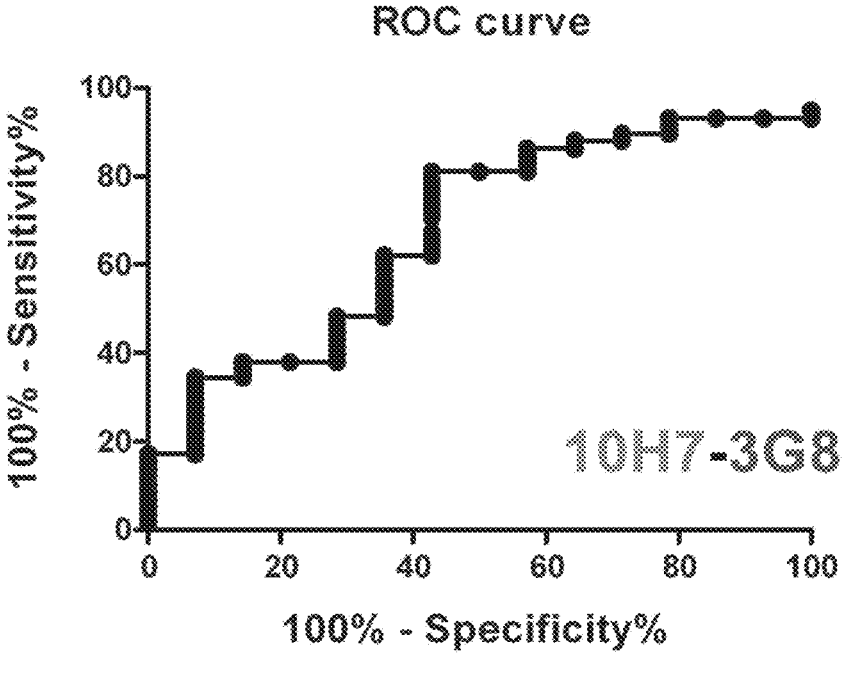

FIGS. 9A, 9B, 9C and 9D show the receiver operating characteristic curves (ROG) and area under the curves (AUG) of respective antibody combinations. FIG. 9A shows the case using 9B12-3G8 antibody combination, FIG. 9B shows the case using 8G4-3G8 antibody combination, FIG. 9C shows the case using 2A11-3F12 antibody combination, and FIG. 9D shows the case using 10H7-3F12 antibody combination.

As shown in FIGS. 9A, 9B, 9C and 9D, when 9B12-3G8, 8G4-3G8, 2A11-3F12, and 10H7-3G8 antibody combinations were used, AUG values were 0.8596, 0.8368, 0.8554, and 0.6736. That is, in the case of all antibody combinations, the AUG values in the ROG curve were around 0.7, and when the 9B12-3G8, 8G4-3G8, and 2A11-3F12 antibody combinations were used, AUG values were measured to be between 0.8 and 0.9. These results show that each antibody combination can be used to diagnose breast cancer by using high sensitivity and specificity. Therefore, the four antibody combinations can be usefully used for diagnosing breast cancer.

A composition for use in diagnosing cancer including an anti-BAG2 antibody or antigen-binding fragment thereof according to one aspect may provide information used for diagnosing cancer.

According to the method of providing information used for diagnosing cancer according to another aspect, unlike the conventional diagnostic method of collecting tissues, the presence or level of BAG2 polypeptide in the blood can be identified or measured from the blood from the blood and diagnostic usefulness is high. Accordingly, various organizations can use the method for the diagnosis of cancer.

[Accession Number]
Depositary: Korea Research Institute of Bioscience and Biotechnology
Accession number: KCTC13737BP
Deposit date: Nov. 28, 2018
Depositary: Korea Research Institute of Bioscience and Biotechnology
Accession number: KCTC13738BP
Deposit date: Nov. 28, 2018
Depositary: Korea Research Institute of Bioscience and Biotechnology
Accession number: KCTC13739BP
Deposit date: Nov. 28, 2018
Depositary: Korea Research Institute of Bioscience and Biotechnology
Accession number: KCTC13740BP Deposit date: Nov. 28, 2018
Depositary: Korea Research Institute of Bioscience and Biotechnology
Accession number: KCTC13741BP
Deposit date: Nov. 28, 2018
Depositary: Korea Research Institute of Bioscience and Biotechnology
Accession number: KCTC13742BP
Deposit date: Nov. 28, 2018
Depositary: Korea Research Institute of Bioscience and Biotechnology
Accession number: KCTC13743BP
Deposit date: Nov. 28, 2018
Depositary: Korea Research Institute of Bioscience and Biotechnology
Accession number: KCTC13744BP
Deposit date: Nov. 28, 2018
Depositary: Korea Research Institute of Bioscience and Biotechnology
Accession number: KCTC13745BP
Deposit date: Nov. 28, 2018
Depositary: Korea Research Institute of Bioscience and Biotechnology
Accession number: KCTC13746BP
Deposit date: Nov. 28, 2018

All of the references cited herein are incorporated by reference in their entirety.

Those skilled in the art will recognize, or be able to ascertain using no more than routine experimentation, many equivalents to the specific embodiments of the invention specifically described herein.

We claim:

1. A composition for use in diagnosing cancer, the composition comprising:

an antibody or antigen-binding fragment thereof comprising a heavy chain variable region comprising VH-CDR1 consisting of the amino acid sequence of SEQ ID NO: 33, VH-CDR2 consisting of the amino acid sequence of SEQ ID NO: 39 in which 6th Xaa and 7th Xaa are each Gly, and VH-CDR3 consisting of the amino acid sequence of SEQ ID NO: 45 and a light chain variable region comprising VL-CDR1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63; and an antibody or antigen-binding fragment thereof comprising a heavy chain variable region comprising a VH-CDR1 consisting of the amino acid sequence of SEQ ID NO: 38, VH-CDR2 consisting of the amino acid sequence of SEQ ID NO: 44, and VH-CDR3 consisting of the amino acid sequence of SEQ ID NO: 50; and a light chain variable region comprising a VL-CDR1 consisting of the amino acid sequence of SEQ ID NO: 56, VL-CDR2 consisting of the amino acid sequence of SEQ ID NO: 62, and VL-CDR3 consisting of the amino acid sequence of SEQ ID NO: 68.

2. The composition of claim 1, wherein the antibody or antigen-binding fragment is labeled with a detectable label or a label capable of emitting a detectable signal.

3. The composition of claim 1, wherein the cancer is breast cancer, colorectal cancer, head and neck cancer, colon cancer, skin cancer, pancreatic cancer, lung cancer, gastric cancer, prostate cancer, bladder cancer, urethral cancer, liver cancer, kidney cancer, clear cell sarcoma, melanoma, cerebrospinal tumor, brain cancer, thymus, mesothelioma, esophageal cancer, bile duct cancer, testicular cancer, germ cell tumor, thyroid cancer, parathyroid cancer, cervical cancer, endometrial cancer, lymphoma, myelodysplastic syndromes (MOS), myelofibrosis, acute leukemia, chronic leukemia, multiple myeloma, Hodgkin's disease, endocrine cancer, or sarcoma.

4. A kit for use in diagnosing cancer, the kit comprising: the composition of claim 1.

5. A composition for use in diagnosing cancer, the composition comprising:

an antibody or antigen-binding fragment thereof comprising a heavy chain variable region comprising VH-CDR1 consisting of the amino acid sequence of SEQ ID NO: 35 in which 2nd Xaa is Tyr, VH-CDR2 consisting of the amino acid sequence of SEQ ID NO: 41 in which 8th Xaa is Ser, and VH-CDR3 consisting of the amino acid sequence of SEQ ID NO: 47 in which 12th Xaa is His and a light chain variable region comprising VL-CDR1 consisting of the amino acid sequence of SEQ ID NO: 53 in which 3rd Xaa is Met, VL-CDR2 consisting of the amino acid sequence of SEQ ID NO: 59 in which 2nd Xaa is Ala, and VL-CDR3 consisting of amino acid sequence of SEQ ID NO: 65; and an antibody or antigen-binding fragment thereof comprising a heavy chain variable region comprising a VH-CDR 1 consisting of the amino acid sequence of SEQ ID NO: 37, VH-CDR2 consisting of the amino acid sequence of SEQ ID NO: 43, and VH-CDR3 consisting of the amino acid sequence of SEQ ID NO: 49; and a light chain variable region comprising a VL-CDR1 consisting of the amino acid sequence of SEQ ID NO: 55, VL-CDR2 consisting of the amino acid sequence of SEQ ID NO: 61, and VL-CDR3 consisting of the amino acid sequence of SEQ ID NO: 67.

6. The composition of claim 5, wherein the antibody or antigen-binding fragment is labeled with a detectable label or a label capable of emitting a detectable signal.

7. The composition of claim 5, wherein the cancer is breast cancer, colorectal cancer, head and neck cancer, colon cancer, skin cancer, pancreatic cancer, lung cancer, gastric cancer, prostate cancer, bladder cancer, urethral cancer, liver cancer, kidney cancer, clear cell sarcoma, melanoma, cerebrospinal tumor, brain cancer, thymus, mesothelioma, esophageal cancer, bile duct cancer, testicular cancer, germ cell tumor, thyroid cancer, parathyroid cancer, cervical cancer, endometrial cancer, lymphoma, myelodysplastic syndromes (MOS), myelofibrosis, acute leukemia, chronic leukemia, multiple myeloma, Hodgkin's disease, endocrine cancer, or sarcoma.

8. A kit for use in diagnosing cancer, the kit comprising: the composition of claim 5.

9. A composition for use in diagnosing cancer, the composition comprising:

an antibody or antigen-binding fragment thereof comprising a heavy chain variable region comprising VH-CDR1 consisting of the amino acid sequence of SEQ ID NO: 33, VH-CDR2 consisting of the amino acid sequence of SEQ ID NO: 39 in which 6th Xaa and 7th Xaa are Ala and Gly, respectively, and VH-CDR3 consisting of the amino acid sequence of SEQ ID NO: 45 and a light chain variable region comprising VL-CDR1 consisting of the amino acid sequence of SEQ ID NO: 51, VL-CDR2 consisting of the amino acid sequence of SEQ ID NO: 57, and VL-CDR3 consisting of the amino acid sequence of SEQ ID NO: 63; and an antibody or antigen-binding fragment thereof comprising a heavy chain variable region comprising a VH-CDR 1 consisting of the amino acid sequence of SEQ ID NO: 37, VH-CDR2 consisting of the amino acid sequence of SEQ ID NO: 43, and VH-CDR3 consisting of the amino acid sequence of SEQ ID NO: 49; and a light chain variable region comprising a VL-CDR1 consisting of the amino acid sequence of SEQ ID NO: 55, VL-CDR2 consisting of the amino acid sequence of SEQ ID NO: 61, and VL-CDR3 consisting of the amino acid sequence of SEQ ID NO: 67.

10. The composition of claim 9, wherein the antibody or antigen-binding fragment is labeled with a detectable label or a label capable of emitting a detectable signal.

11. The composition of claim 9, wherein the cancer is breast cancer, colorectal cancer, head and neck cancer, colon cancer, skin cancer, pancreatic cancer, lung cancer, gastric cancer, prostate cancer, bladder cancer, urethral cancer, liver cancer, kidney cancer, clear cell sarcoma, melanoma, cerebrospinal tumor, brain cancer, thymus, mesothelioma, esophageal cancer, bile duct cancer, testicular cancer, germ cell tumor, thyroid cancer, parathyroid cancer, cervical cancer, endometrial cancer, lymphoma, myelodysplastic syndromes (MOS), myelofibrosis, acute leukemia, chronic leukemia, multiple myeloma, Hodgkin's disease, endocrine cancer, or sarcoma.

12. A kit for use in diagnosing cancer, the kit comprising: the composition of claim 9.

13. A composition for use in diagnosing cancer, the composition comprising:

an antibody or antigen-binding fragment thereof comprising a heavy chain variable region comprising a VH-CDR 1 consisting of the amino acid sequence of SEQ ID NO: 38, VH-CDR2 consisting of the amino acid sequence of SEQ ID NO: 44, and VH-CDR3 consisting of the amino acid sequence of SEQ ID NO: 50; and a light chain variable region comprising a VL-CDR1 consisting of the amino acid sequence of SEQ ID NO: 56, VL-CDR2 consisting of the amino acid sequence of SEQ ID NO: 62, and VL-CDR3 consisting of the amino acid sequence of SEQ ID NO: 68; and an antibody or antigen-binding fragment thereof comprising a heavy chain variable region comprising a VH-CDR 1 consisting of the amino acid sequence of SEQ ID NO: 37, VH-CDR2 consisting of the amino acid sequence of SEQ ID NO: 43, and VH-CDR3 consisting of the amino acid sequence of SEQ ID NO: 49; and a light chain variable region comprising a VL-CDR1 consisting of the amino acid sequence of SEQ ID NO: 55, VL-CDR2 consisting of the amino acid sequence of SEQ ID NO: 61, and VL-CDR3 consisting of the amino acid sequence of SEQ ID NO: 67.

14. The composition of claim 13, wherein the antibody or antigen-binding fragment is labeled with a detectable label or a label capable of emitting a detectable signal.

15. The composition of claim 13, wherein the cancer is breast cancer, colorectal cancer, head and neck cancer, colon cancer, skin cancer, pancreatic cancer, lung cancer, gastric cancer, prostate cancer, bladder cancer, urethral cancer, liver cancer, kidney cancer, clear cell sarcoma, melanoma, cerebrospinal tumor, brain cancer, thymus, mesothelioma, esophageal cancer, bile duct cancer, testicular cancer, germ cell tumor, thyroid cancer, parathyroid cancer, cervical cancer, endometrial cancer, lymphoma, myelodysplastic syndromes (MOS), myelofibrosis, acute leukemia, chronic leukemia, multiple myeloma, Hodgkin's disease, endocrine cancer, or sarcoma.

16. A kit for use in diagnosing cancer, the kit comprising: the composition of claim 13 .

\* \* \* \* \*